US012329460B2

(12) United States Patent
Isola et al.

(10) Patent No.: US 12,329,460 B2
(45) Date of Patent: Jun. 17, 2025

(54) DETERMINING ABLATION PROBE CONFIGURATION

(71) Applicant: KONINKLIJKE PHILIPS N.V., Eindhoven (NL)

(72) Inventors: Alfonso Agatino Isola, Eindhoven (NL); Christoph Neukirchen, Aachen (DE); Marco Baragona, Delft (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 357 days.

(21) Appl. No.: 17/634,704

(22) PCT Filed: Aug. 3, 2020

(86) PCT No.: PCT/EP2020/071762
§ 371 (c)(1),
(2) Date: Feb. 11, 2022

(87) PCT Pub. No.: WO2021/032449
PCT Pub. Date: Feb. 25, 2021

(65) Prior Publication Data
US 2022/0265359 A1 Aug. 25, 2022

(30) Foreign Application Priority Data
Aug. 16, 2019 (EP) .................................. 19192015

(51) Int. Cl.
*A61B 34/10* (2016.01)
*A61B 18/02* (2006.01)
(Continued)

(52) U.S. Cl.
CPC .............. *A61B 34/10* (2016.02); *A61B 18/02* (2013.01); *A61B 18/12* (2013.01); *A61B 18/18* (2013.01);
(Continued)

(58) Field of Classification Search
CPC ......... A61B 34/10; A61B 18/02; A61B 18/12; A61B 18/18; A61B 2034/104;
(Continued)

(56) References Cited

U.S. PATENT DOCUMENTS

2009/0044149 A1* 2/2009 Deguy .................. G06T 11/001
715/853
2011/0015628 A1 1/2011 Dalal
(Continued)

FOREIGN PATENT DOCUMENTS

EP 2373241 B1 1/2015
WO WO2013014648 A1 1/2013

OTHER PUBLICATIONS

PCT International Search Report, International application No. PCT/EP2020/071762, Sep. 4, 2020.
(Continued)

*Primary Examiner* — Rochelle D Turchen

(57) ABSTRACT

Disclosed herein is a medical system (100, 300) comprising a processor (104). Execution of the machine executable (112) instructions causes a processor (104) to: receive (200) three-dimensional medical image data (114) descriptive of a subject (318); receive (202) a desired ablation volume (116), wherein the desired ablation volume is registered to the three-dimensional medical image data; receive (204) one or more protected volumes (118); generate (206) a discrete set of ablation probe positions (120); receive (208) a discrete set of ablation patterns (130); initialize (210) a composite ablation binary mask (122); and initialize (212) a sequential ablation probe configuration list (124). Execution of the machine executable instructions further causes the processor to iteratively generate the sequential ablation probe configuration list by repeatedly: determining (214) an unablated volume (126) by comparing the composite ablation binary mask to the desired ablation volume; determining (216) a
(Continued)

chosen ablation probe configuration (128) using a chosen objective function (132) dependent upon the one or more protected volumes, the unablated volume, the discrete set of ablation patterns, and the discrete set of ablation probe positions; update (218) the composite ablation binary mask by calculating a union between the composite ablation binary mask and the one of the discrete set of ablation patterns located at the one of the discrete set of ablation probe positions; and add (220) the chosen ablation probe configuration to the sequential ablation probe configuration list.

15 Claims, 25 Drawing Sheets

(51) Int. Cl.
    *A61B 18/12*     (2006.01)
    *A61B 18/18*     (2006.01)
    *A61B 34/20*     (2016.01)

(52) U.S. Cl.
    CPC ... *A61B 2034/104* (2016.02); *A61B 2034/105* (2016.02); *A61B 2034/107* (2016.02); *A61B 2034/2051* (2016.02)

(58) Field of Classification Search
    CPC ........ A61B 2034/105; A61B 2034/107; A61B 2034/2051
    See application file for complete search history.

(56) References Cited

U.S. PATENT DOCUMENTS

| | | |
|---|---|---|
| 2014/0058387 A1 | 2/2014 | Kruecker |
| 2016/0270862 A1 | 9/2016 | Fuchs |
| 2020/0179051 A1* | 6/2020 | Miga ...................... G16H 80/00 |

OTHER PUBLICATIONS

Yaniv Z. et al., "Needle-Based Interventions With the Image-Guided Surgery Toolkit (IGSTK): From Phantoms to Clinical Trials", IEEE Transactions on Biomedical Engineering, IEEE Service Center, Piscataway, NJ, USA, vol. 57, No. 4, Nov. 17, 2009, pp. 922-933, XP011343207.

Fusco G. et al., "Selection and Orientation of Directional Sensors for Coverage Maximization", Sensor, Mesh and Ad Hoc Communications and Networks, 2009. SECON '09. 6th Annual IEEE Communications Society Conference on, IEEE, Piscataway, NJ, USA, Jun. 22, 2009, pp. 1-9, XP031493104.

Horster E. et al., "On the Optimal Placement of Multiple Visual Sensors", VSSN '06 : 4th ACM International Workshop on Video Surveillance and Sensor Networks, (Santa Barbara, Calif.) : Oct. 23-27, 2006, ACM, New York, NY, USA, Oct. 27, 2006, pp. 111-120, XP058107239.

Simone B. et al., "Sensor Placement Optimization in Buildings", Image Processing: Machine Vision Applications V, SPIE, 1000 20th St. Bellingham WA 98225-6705 USA, vol. 8300, No. 1, Feb. 9, 2012, pp. 1-13, XP060002145.

Amica™ Probe (14G) Coaugulative Performance in Room Temperature Ex-Vivo Bovine Liver, Vendor Information Sheet for Amica RF Device, Data on file at HS Hospital Service S.p.A. http://www.hshospitalservice.com/.

Cormen T.H. et al., "The Set-Covering Problem", Introduction to Algorithms 3rd Edition, MIT Press and McGraw-Hill, Chapter 35.3, pp. 1117-1122, 2009.

Sadaowski et al., "Exploring Trade-Offs Between Target Coverage, Healthy Tissue Sparing, and the Placement of Catheters in HDR Brachytherapy for Prostate Cancer using a Novel Multi-Objective Model-Based Mixed-Integer Evolutionary Algorithm", GECCO '17: Proceedings of the Genetic and Evolutionary Computation Conference, Jul. 2017, pp. 1224-1231.

Lampinen J. et al., "Mixed Integer-Discrete-Continuous Optimization by Differential Evolution", Proceedings of Mendel'99, 5th International Mendel Conference on Soft Computing, Jun. 9-12, 1999, pp. 71-76.

Ferris M.C. et al., "Radiation Treatment Planning: Mixed Integer Programming Formulations and Approaches", Handbook on Modelling for Discrete Optimization. International Series in Operations Research & Management Science, vol. 88. Springer, Boston, MA., Oct. 2002.

\* cited by examiner

DETERMINING ABLATION PROBE CONFIGURATION

CROSS-REFERENCE TO RELATED APPLICATIONS

This patent application claims the priority benefit under 35 U.S.C. § 371 of International Patent Application no. PCT/EP2020/071762, filed Aug. 3, 2020, which claims the benefit of European Patent Application No. EP19192015.6, filed on Aug. 16, 2019. These applications are hereby incorporated by reference herein in their entirety.

TECHNICAL FIELD

The invention relates to ablation probes, in particular to the placement of ablation probes.

BACKGROUND OF THE INVENTION

Ablation probes may be used to treat tumors through ablation. For example, there are microwave ablation probes, thermal ablation probes, cryoablation probe, focused ultrasound ablation probes, and others. In particular, thermal ablation cancer treatments are becoming increasingly popular due to their applicability to non-resectable tumors and the rapid recovery of the patient.

United States patent application publication US2014058387 A1 discloses a system and method for ablation planning includes defining shapes and sizes for one or more ablation volumes based on probability of treatment, and determining a target volume to be treated. A procedure plan is provided by determining a number and location of planned ablations within the target volume using the one or more ablation volumes. A joint probability distribution is determined for at least two planned ablations in the target volume. A final configuration is visualized to determine if plan objectives are met based on a probability of treatment for the target volume.

SUMMARY OF THE INVENTION

The invention provides for a medical system, a computer program product, and a method in the independent claims. Embodiments are given in the dependent claims.

A difficulty in planning ablation procedures is that the probes can be positioned freely and may often times have a continuously variable power supplied to them. It can be extremely difficult to properly plan the placement of ablation probes. Embodiments may provide for a system that improves determining the position of ablation probes. This for example may be provided in the form of a sequential ablation probe configuration list that may be displayed as a list or displayed graphically.

This may be achieved by receiving three-dimensional medical image data, a desired ablation volume, and a set of one or more protected volumes. The system then creates a set of discrete ablation probe positions and receives a discrete set of ablation patterns. A chosen objective function is used to evaluate each of the discrete set of ablation patterns at each of the set of discrete set of ablation probe positions. The chosen objective function is then used to choose the probe position and ablation pattern. This is then performed repeatedly to make sequential ablation probe configuration list. This may have the advantage that multiple types of ablation probes and configurations may be considered which would be impossible for an algorithm which performs a continuous optimization.

In one aspect the invention provides for a medical system that comprises a memory which stores machine-executable instructions and a processor which is configured for controlling the medical system. Execution of the machine-executable instructions causes the processor to receive three-dimensional medical image data descriptive of a subject. Execution of the machine-executable instructions further causes the processor to receive a desired ablation volume. The term desired ablation volume is a label for a particular ablation volume. The desired ablation volume is registered to the three-dimensional medical image data. That is to say the desired ablation volume marks a region or identifies a region of the three-dimensional medical image data.

Execution of the machine-executable instructions further causes the processor to receive one or more protected volumes. The one or more protected volumes are registered to the three-dimensional medical image data. The one or more protected volumes may for example be volumes which could injure the subject if they are sonicated or ablated too much. For example, the one or more protected volumes may be used to protect organs or critical anatomical structures.

Execution of the machine-executable instructions further causes the processor to generate a discrete set of ablation probe positions registered to the three-dimensional medical image data. But normally when ablation probes are positioned there is a free choice as to the position and orientation. In this case the locations around the desired ablation volume may be used to generate a pattern or set of discrete ablation probe positions. These for example could be generated using a predetermined pattern or algorithm for generating the discrete set. Execution of the machine-executable instructions further causes the processor to receive a discrete set of ablation patterns.

The discrete set of ablation patterns comprises multiple ablation patterns. The discrete set of ablation patterns could be ablation patterns for a single ablation probe, for example oriented in different directions and/or with different amounts of power supply. In other examples the discrete set of ablation patterns may be from multiple ablation probes. Execution of the machine-executable instructions further cause the processor to initialize a composite ablation binary mask registered to the three-dimensional medical imaging data. For example, the step of initializing the composite ablation binary mask may be to create a blank or unused composite ablation binary mask. The term composite ablation binary mask is used to identify a particular binary mask. The composite ablation binary mask in this case is an ablation binary mask that stores the composite or intersection of all the ablation patterns that are used.

Execution of the machine-executable instructions further cause the processor to initialize a sequential ablation probe configuration list. Initially the sequential ablation probe configuration list may be empty. As the algorithm continues the different ablation probe configurations are added to the sequential ablation probe configuration list.

Execution of the machine-executable instructions further cause the processor to generate the sequential ablation probe configuration list by first determining an unablated volume by comparing the composite ablation binary mask to the desired ablation volume. The unablated volume is registered to the three-dimensional medical image data. The composite ablation binary mask may be used to identify regions that have already been ablated or are intended to be ablated using the configurations on the sequential ablation probe configuration list. A comparison between the desired ablation volume and the composite ablation binary mask can be used to find a region which still needs to be ablated or additional probes added so that ablation occurs.

Execution of the machine-executable instructions further cause the processor to generate the sequential ablation probe configuration list by determining a chosen ablation probe configuration using a chosen objective function dependent upon the one or more protected volumes, the unablated volume, the discrete set of ablation patterns, and the discrete set of ablation probe positions. The chosen ablation probe configuration specifies one of the discrete set of ablation probe positions and one of the discrete set of ablation patterns. In this step a chosen objective function can be used to evaluate the various combinations of the discrete set of ablation patterns in each of the discrete set of ablation probe positions.

The chosen objective function is used to choose the best choice. The chosen objective function may be used to objectively measure such things as coverage of the unablated volume as well as avoiding the one or more protected volumes.

The chosen ablation probe configuration specifies one of the discrete set of ablation probe positions and one of the discrete set of ablation patterns. Execution of the machine-executable instructions further cause the processor to generate the sequential ablation probe configuration list by updating the composite ablation binary mask by calculating a union between the composite ablation binary mask and the one of the discrete set of ablation patterns located at the one of the discrete set of ablation probe positions. After the chosen ablation probe configuration is done this choice is then used to update the composite ablation binary mask to indicate which region this chosen ablation probe then ablates. Execution of the machine-executable instructions further cause the processor to generate the sequential ablation probe configuration list by adding the chosen ablation probe configuration to the sequential ablation probe configuration list.

Execution of the machine-executable instructions further cause the processor to repeatedly generate the sequential ablation probe configuration list until one or more of a predetermined set of criteria is satisfied. For example, the operator could specify that a maximum number of ablation probes are used. After a maximum number of the discrete set of ablation patterns is added to the chosen ablation probe configuration then the method may stop. Other criteria may be used such as specifying a minimum amount of the desired ablation volume which is covered by the composite ablation binary mask. Another criteria may be a maximum amount of the one or more protected volumes being ablated. In some instances, the method may also prevent any of the one or more protected volumes from being ablated.

This medical system may be beneficial because it may provide for a very effective means of determining the position of ablation probes for performing an ablation of the desired ablation volume. The method uses discrete locations for positioning the ablation probes in the form of the discrete set of ablation probe positions and also a discrete amount of ablation patterns. This may for example not reach the optimum solution but very computationally efficiently it arrives at a solution which is very close to any optimum. This for example has the benefit that a larger variety of ablation probes can be rapidly considered and used to assemble the ablation probe configurations for a particular subject.

The above embodiment applies to both multiple ablation probes being inserted into a subject at the same time and also to ablation probes which are inserted sequentially. Both the use of the chosen objective function may be interpreted as solving an optimization problem formulated using the objective function.

In another embodiment execution of the machine-executable instructions further causes the processor to update the sequential ablation probe configuration list by iteratively assigning each one of the discrete set of ablation probe positions to a spatially continuous probe position and then modifying the spatially continuous probe position using a second objective function. In this embodiment the determination of the sequential ablation probe configuration list is performed in two major steps. In the first step the probe positions and the discrete set of ablation patterns are first determined. In a second step the discrete set of ablation probe configurations is then modified to be spatially continuous and each one of these is then iteratively improved. This embodiment may be beneficial because it may provide a sequential ablation probe configuration list that is very close to the optimum with an extremely fast and efficient numerical method.

The second objective function may either be identical with the chosen objective function or it may be a different objective function.

In another embodiment the spatially continuous probe position is a spatially continuous linear position and/or a spatially continuous rotation. In this embodiment the spatially continuous probe position may for example be how far the ablation probe is moved in a linear direction and/or how far it is rotated. This may further aid in optimizing the sequential ablation probe configuration list.

In another embodiment the medical system further comprises a display. Execution of the machine-executable instructions further cause the processor to display the sequential ablation probe configuration list on the display. This may be beneficial because a medical practitioner may then have the sequential ablation probe configuration list in a format which may enable the medical practitioner to use ablation probes to fulfill it.

In another embodiment the sequential ablation probe configuration list is a list of grid locations and insertion depths for an indexed ablation probe insertion block. An indexed ablation probe insertion block as used herein is a structure or guide which is external to a subject and is mounted in a fixed position with respect to the subject. The medical practitioner can choose one of a number of different guides into which an ablation probe can be inserted. These for example may be assigned an index value or label. The medical practitioner can then insert the ablation probe at a particular depth into the indexed ablation probe insertion block. Providing a list of grid locations and insertion depths then provides an easy guide for the medical practitioner to insert ablation probes in the proper position in the subject. This for example may be done sequentially or it may be done with more than one probe at the same time.

In another embodiment the sequential ablation probe configuration list is displayed as an illustration of free position of ablation probes specified in the sequential ablation probe configuration list. For example, the illustration of the free position of the ablation probes may be superimposed on a medical image. This may be useful for a medical practitioner to position the ablation probes properly.

In another embodiment the medical system further comprises a medical imaging system configured for acquiring the three-dimensional medical image data. Execution of the machine-executable instructions further causes the processor to control the medical imaging system to acquire the three-dimensional medical image data. This for example may be beneficial because the medical system has a means of both measuring the internal anatomy of a subject as well as specifying the location of the ablation probes.

In another embodiment the medical imaging system is a magnetic resonance imaging system.

In another embodiment the medical imaging system is an ultrasound system.

In another embodiment the medical imaging system is a computed tomography system.

In another embodiment execution of the machine-executable instructions further causes the processor to control the medical imaging system to acquire the real-time ablation probe tracking data. Execution of the machine-executable instructions further cause the processor to determine an ablation probe position registered to the three-dimensional medical image data using the real-time ablation probe tracking data. Execution of the machine-executable instructions further cause the processor to render the ablation probe position superimposed on the three-dimensional medical image data using the display in real time. This embodiment may be beneficial because it may provide for a means of not only specifying the position of the ablation probes but actually showing where the ablation probe is as the medical practitioner inserts it. This may aid the medical practitioner in properly positioning ablation probes.

In another embodiment execution of the machine-executable instructions further causes the processor to determine a measured position for the chosen ablation probe configuration of the sequential ablation probe configuration list. Execution of the machine-executable instructions further causes the processor to recalculate the sequential ablation probe configuration list using the measured position as a fixed position. In this embodiment the medical imaging system measures the actual position that an ablation probe is placed; this is the measured position. This then provides more detailed information on where the ablation actually takes place. In this case the sequential ablation probe configuration list is then recalculated using the actual measured position for the chosen ablation probe. This embodiment may be beneficial because it may aid in more effectively ablating the desired ablation volume.

In another embodiment execution of the machine-executable instructions further causes the processor to measure an ablated volume using the medical imaging system. Execution of the machine-executable instructions further causes the processor to correct the desired ablation volume by removing the ablation volume from the desired ablation volume. Execution of the machine-executable instructions further cause the processor to recalculate the sequential ablation probe configuration list using the corrected desired ablation volume. This embodiment may be beneficial because the actual ablated volume is measured as opposed to an indirect quantity such as the position of the ablation probe. This may be beneficial because in some cases the tissue may behave differently than the patterns indicated in the discrete set of ablation patterns.

For example, for measuring the ablated volume may be done in different ways using different types of medical imaging systems. For example, if the medical imaging system is a magnetic resonance image the magnetic resonance imaging system may for example be able to measure the spatially dependent temperature of the subject as a function of time. Other medical imaging techniques may for example examine or detect damage caused by the ablation. For example, if tissue is damaged its form within an ultrasonic scan may vary from unsonicated tissue.

In another embodiment the chosen objective function comprises a quadratic ablation coverage-based objective function, a minimum/maximum ablation coverage function, and a uniform quadratic coverage function. Use of any of these functions may be beneficial because they are effective at both choosing regions to ablate as well as protecting critical regions which are specified in the one or more protected volumes.

In another embodiment the predetermined set of criteria comprises a maximum number of allowed ablation probes.

In another embodiment the predetermined set of criteria comprises an ablation coverage goal of the desired ablation volume. For example, if the ablation coverage goal of the desired volume is reached or exceeded then the ablation can be stopped.

In another embodiment the discrete set of ablation patterns comprises ablation patterns for cryo-ablation probes.

In another embodiment the discrete set of ablation patterns comprises ablation patterns for laser ablation probes.

In another embodiment the discrete set of ablation patterns comprises ablation patterns for microwave ablation probes.

In another embodiment the discrete set of ablation patterns comprises ablation patterns for focused ultrasound ablation probes.

In another embodiment the discrete set of ablation patterns comprises ablation patterns for radio-frequency ablation probes.

In another embodiment the discrete set of ablation patterns comprises ablation patterns for irreversible electroporation probes.

In another aspect the invention provides for a computer program product comprising machine-executable instructions for execution by a processor controlling the medical system. Execution of the machine-executable instructions causes the processor to receive three-dimensional medical image data descriptive of a subject. Execution of the machine-executable instructions further causes the processor to receive a desired ablation volume. The desired ablation volume is registered to the three-dimensional medical image data. Execution of the machine-executable instructions further causes the processor to receive one or more protected volumes. The one or more protected volumes are registered to the three-dimensional medical image data.

Execution of the machine-executable instructions further cause the processor to generate a discrete set of ablation probe positions registered to the three-dimensional medical image data. Execution of the machine-executable instructions further causes the processor to receive a discrete set of ablation patterns. The discrete set of ablation patterns comprises multiple ablation patterns. Execution of the machine-executable instructions further causes the processor to initialize a composite ablation binary mask registered to the three-dimensional medical image data. Execution of the machine-executable instructions further cause the processor to initialize a sequential ablation probe configuration list.

Execution of the machine-executable instructions further causes the processor to generate the sequential ablation probe configuration list by determining an unablated volume by comparing the composite ablation binary mask to the desired ablation volume. The unablated volume is registered to the three-dimensional medical image data. Execution of the machine-executable instructions further cause the processor to generate the sequential ablation probe configuration list by determining a chosen ablation probe configuration using a chosen objective function dependent upon the one or more protected volumes, the unablated volume, the discrete set of ablation patterns, and the discrete set of ablation probe positions. The chosen ablation probe configuration specifies one of the discrete sets of ablation probe positions and one of the discrete set of ablation patterns.

Execution of the machine-executable instructions further causes the processor to generate the sequential ablation probe configuration list by updating the composite ablation binary mask by calculating a union between the composite ablation binary mask and the one or more of the discrete sets of ablation patterns located at the one of the discrete set of ablation probe positions. Execution of the machine-executable instructions further cause the processor to generate the sequential ablation probe configuration list by adding the chosen ablation probe configuration to the sequential ablation probe configuration list. Execution of the machine-executable instructions further causes the processor to repeatedly generate the sequential ablation probe configuration list until one or more of a predetermined set of criteria is satisfied. The advantages of this embodiment have been previously discussed.

In another aspect the invention provides for a method of operating a medical system. The method comprises receiving three-dimensional medical image data descriptive of a subject. The method further comprises receiving a desired ablation volume. The desired ablation volume is registered to the three-dimensional medical image data. The method further comprises receiving one or more protected volumes, wherein the one or more protected volumes are registered to the three-dimensional medical image data. The method further comprises generating a discrete set of ablation probe positions registered to the three-dimensional medical image data. The method further comprises receiving a discrete set of ablation patterns. The discrete set of ablation patterns comprises multiple ablation patterns. The method further comprises initializing a composite ablation binary mask registered to the three-dimensional medical image data. The method further comprises initializing a sequential ablation probe configuration list. The method further comprises generating the sequential ablation probe configuration list by determining an unablated volume by comparing the composite ablation binary mask to the desired ablation volume. The unablated volume is registered to the three-dimensional medical image data.

The method further comprises generating the sequential ablation probe configuration list by determining a chosen ablation probe configuration using a chosen objective function dependent upon the one or more protected volumes, the unablated volume, the discrete set of ablation patterns, and the discrete set of ablation probe positions. The chosen ablation probe configuration specifies one of the discrete set of ablation probe positions and one of the discrete set of ablation patterns. The method further comprises generating the sequential ablation probe configuration list by updating the composite ablation binary mask by calculating a union between the composite ablation binary mask and the one of the discrete set of ablation patterns located at the one of the discrete set of ablation probe positions.

The method further comprises generating the sequential ablation probe configuration list by adding the chosen ablation probe configuration to the sequential ablation probe configuration list. The method further comprises repeatedly generating sequential ablation probe configuration list until one or more of a predetermined set of criteria is satisfied. The advantages of this embodiment have been previously discussed. It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments, computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Three-dimensional medical image data is defined herein as being the reconstructed three-dimensional data representing a visualization of anatomic data. A visualization can be performed using a computer.

Magnetic Resonance (MR) imaging data is defined herein as being the recorded measurements of radio frequency signals emitted by atomic spins using the antenna of a Magnetic resonance apparatus during a magnetic resonance imaging scan. A Magnetic Resonance Imaging (MM) image or MR image is defined herein as being the reconstructed two- or three-dimensional visualization of anatomic data contained within the magnetic resonance imaging data. A magnetic resonance image may be an example of two- or three-dimensional medical image data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
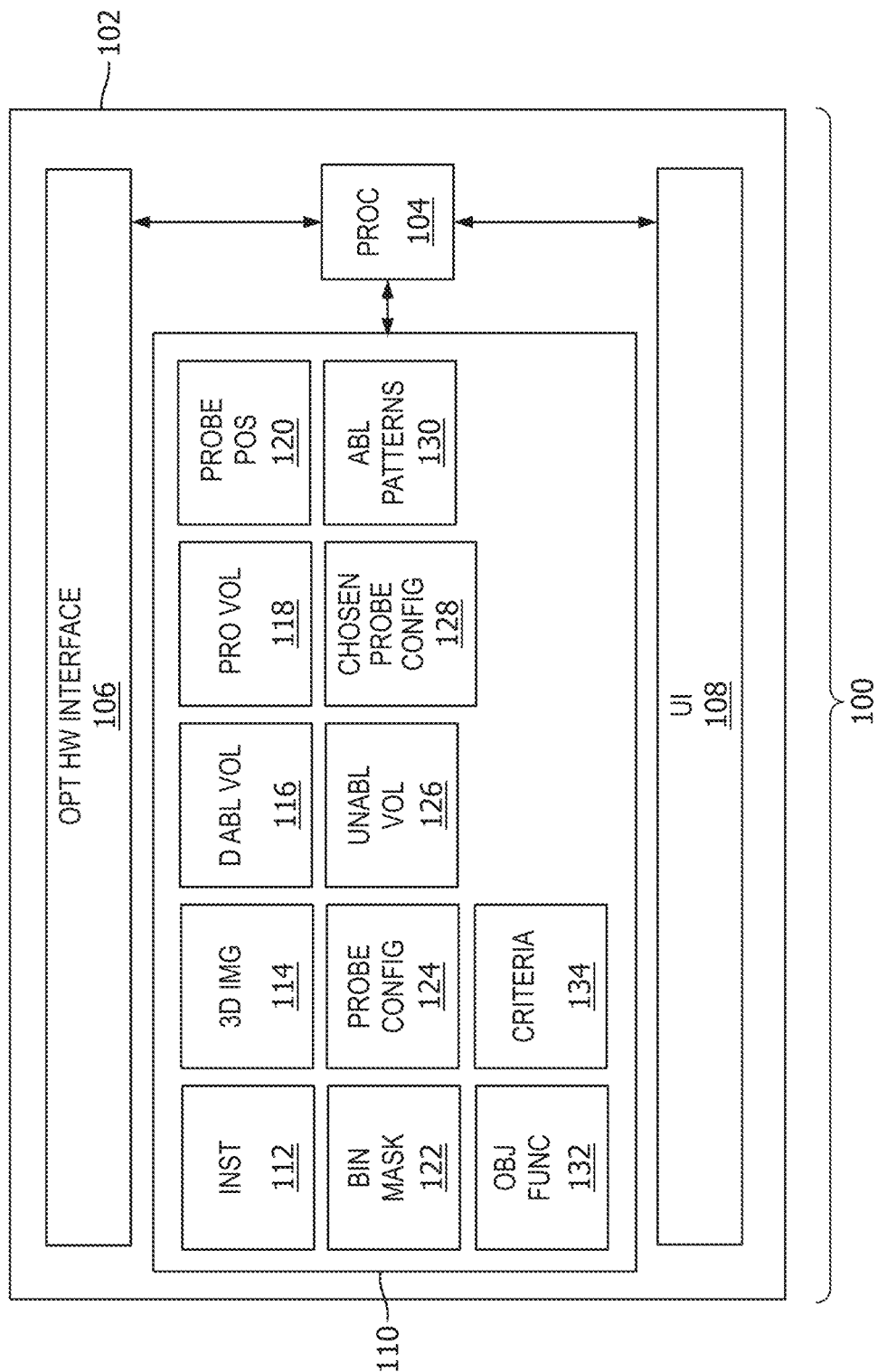
FIG. 1 illustrates an example of a medical system.

FIG. 1 illustrates an example of a medical system 100. The medical system 100 is shown as comprising a computer 102 that has a processor 104. The processor 104 is intended to represent one or more processors with one or more cores. The processor 104 is shown as being within a single computer 102 but may also be distributed amongst multiple computer systems. The processor is further shown as being connected to an optional hardware interface 106, a user interface 108, and a memory 110. The hardware interface 106 may enable the processor 104 to communicate with other components of the medical system. For example, if the medical system 100 comprises a medical imaging system the hardware interface 106 may enable the processor 104 to control and operate the medical imaging system. The user interface 108 may be a user interface which enables a user or operator to interact with the medical system 100. For example, the user interface 108 may comprise a display. The memory 110 may be any combination of memory which is accessible to the processor 104. This may include such things as main memory, cached memory, and also non-volatile memory such as flash RAM, hard drives, or other storage devices. In some examples the memory 110 may be considered to be a non-transitory computer-readable medium.

The memory 110 is shown as containing machine-executable instructions 112. The machine-executable instructions 112 enable the processor 104 to perform basic data processing techniques and also to control other components of the medical system 100 if they are present. The memory 110 is further shown as containing three-dimensional medical image data 114. The memory 110 is further shown as containing a desired ablation volume 116. The desired ablation volume 116 is registered to the three-dimensional medical image data 114. The memory 110 is further shown as containing one or more protected volumes 118. The one or more protected volumes 118 are also registered to the three-dimensional medical image data 114. The one or more protected volumes 118 may represent organs or sensitive anatomical structures of the subject which should not be ablated. The memory 110 is further shown as containing a discrete set of ablation probe positions 120. These are locations within the three-dimensional medical image data 114 where ablation probes can be placed.

The memory 110 is further shown as containing a composite ablation binary mask 122. The composite ablation binary mask 122 is a binary mask which is used to illustrate all the various locations where multiple ablation probes performed an ablation. It can be used to keep track of the volume which should be ablated. The memory 110 is further shown as containing a sequential ablation probe configuration list 124. The sequential ablation probe configuration list 124 contains a list of ablation probe positions and profiles. The individual profiles may correspond to the choice of a particular ablation probe as well as a particular power configuration for that ablation probe.

The memory 110 is further shown as containing an unablated volume 126. The unablated volume is the desired ablation volume 116 minus the composite ablation binary mask 122. This is the volume that still needs to be ablated. The memory 110 is further shown as containing a chosen ablation probe configuration 128. The chosen ablation probe configuration 128 is a choice of a location selected from the discrete set of ablation probe positions 120 and one of a set of ablation patterns 130. The set of ablation patterns 130 are also shown as being stored within the memory 110. The set of ablation patterns 130 may for example indicate a choice of a particular ablation probe as well as an operational mode of this ablation probe. For example, the power could be selected by having multiple ablation patterns for the same ablation probe with differing amounts of power and or duration.

The memory 110 is further shown as containing a chosen objective function 132. The chosen objective function 132 is dependent on the one or more protected volumes 118 and the unablated volume 126. It is then used to evaluate each of the set of ablation patterns 130 and each of the discrete set of ablation probe positions 120. For example, an optimization program can be used to choose the best solution. The memory 110 is further shown as containing a predetermined set of criteria 134 that are used to halt the selection of more probes for the sequential ablation probe configuration list 124.

Figure 2:
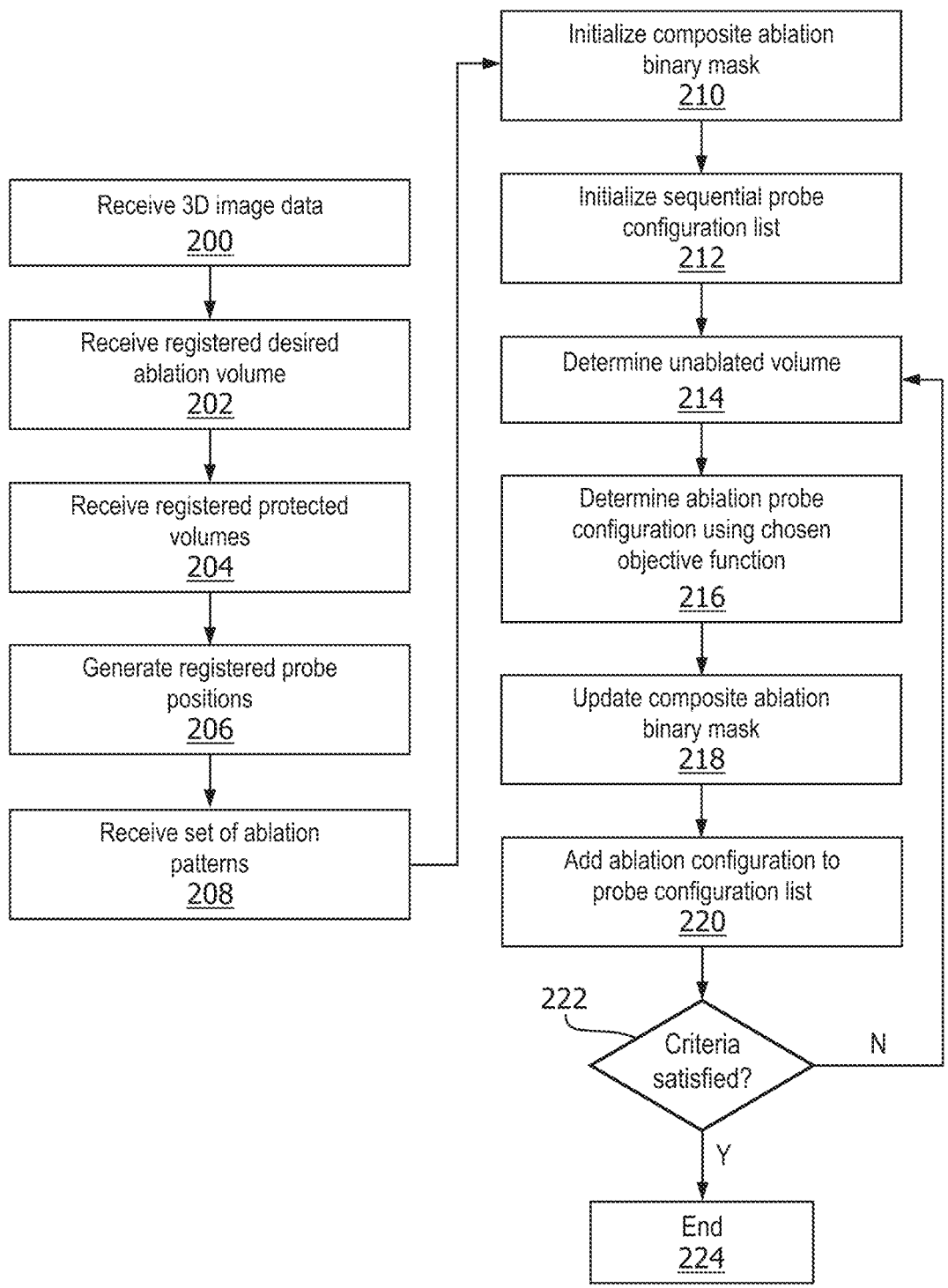
FIG. 2 shows a flow chart which illustrates a method of operating the medical system of FIG. 1.

FIG. 2 shows a flowchart which illustrates a method of operating the medical system 100 of FIG. 1. First in step 200 the three-dimensional medical image data 114 which is descriptive of the subject is received. Next in step 202 the desired ablation volume 116 is received. Then in step 204 the one or more protected volumes 118 are received. Then in step 206 the discrete set of ablation probe positions is generated. In step 210 the composite ablation binary mask 122 is initialized. Then in step 212 the sequential ablation probe configuration list 124 is initialized.

Steps 214, 216, 218, and 220 are performed iteratively. In step 214 the unablated volume 126 is determined by comparing the composite ablation binary mask 122 and the desired ablation volume 116. For example, the composite ablation binary mask 122 can be used to determine which part of the desired ablation volume 116 has not yet been ablated. Then in step 216 the chosen objective function 132 is used to determine a chosen ablation probe configuration 128. The chosen objective function uses the unablated volume 126 and the one or more protected volumes 118 and then tries each of the discrete set of ablation patterns 130 at each of the discrete set of ablation probe positions 120. The best solution is selected and this is used as the chosen ablation probe configuration 128.

Then in step 218 the composite ablation binary mask 122 is updated by calculating a union between the composite ablation binary mask 122 and the one of the discrete set of ablation patterns located at the one of the discrete set of ablation probe positions. Then in step 220 the chosen ablation probe configuration is added to the sequential ablation probe configuration list. The method then proceeds to step 222 which is a question box and the question is are any of the predetermined set of criteria satisfied. If the answer is yes then the method proceeds to step 224 and the method ends. If the answer is no then the method proceeds back to step 214 and the iterative process is repeated again. It should be noted that each time through the list the composite ablation binary mask 122 will mark off a larger volume of the desired ablation volume 116.

Figure 3:
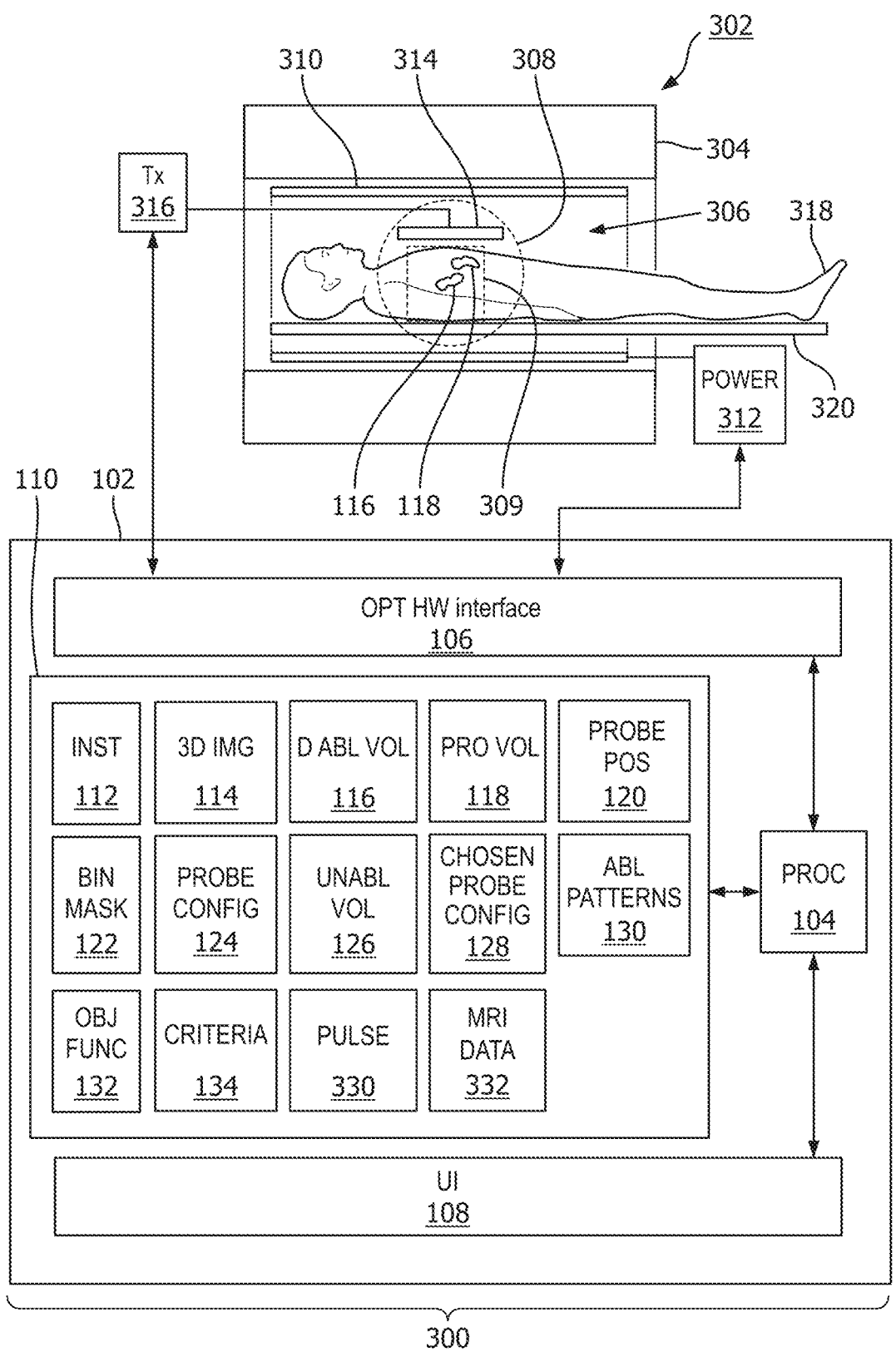
FIG. 3 illustrates a further example of a medical system.

FIG. 3 illustrates a further example of a medical system 300. The medical system 300 is similar to the medical system 100 illustrated in FIG. 1 except that it additionally contains a magnetic resonance imaging system 302.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. A field of view 309 is shown within the imaging zone 308. The magnetic resonance data that is acquired typically acquired for the field of view 309. A subject 318 is shown as being supported by a subject support 320 such that at least a portion of the subject 318 is within the imaging zone 308 and the field of view 309. Within the imaging zone 308 there can be seen the desired ablation volume 116 and one protected volume 118

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The transceiver 316 and the gradient controller 312 are shown as being connected to the hardware interface 106 of a computer system 102. The memory 110 is further shown as containing pulse sequence commands 330. The pulse sequence commands 330 are commands or data which can be converted into commands which enable the processor 104 to control the operation of the magnetic resonance imaging system 302. The memory 110 is further shown as containing magnetic resonance imaging data 332 that has been acquired by controlling the magnetic resonance imaging system 302 with the pulse sequence commands 330.

The medical system 300 depicted in FIG. 3 can be modified in a variety of ways. A system can be used to track the location of ablation probes as they are inserted into the subject 318. For example, a fiducial marker may be incorporated into the tip or other region of an ablation probe. Additionally, the magnetic resonance imaging system 302 can be modified with specialized pulse sequence commands to measure the temperature within the subject 318.

Figure 4:
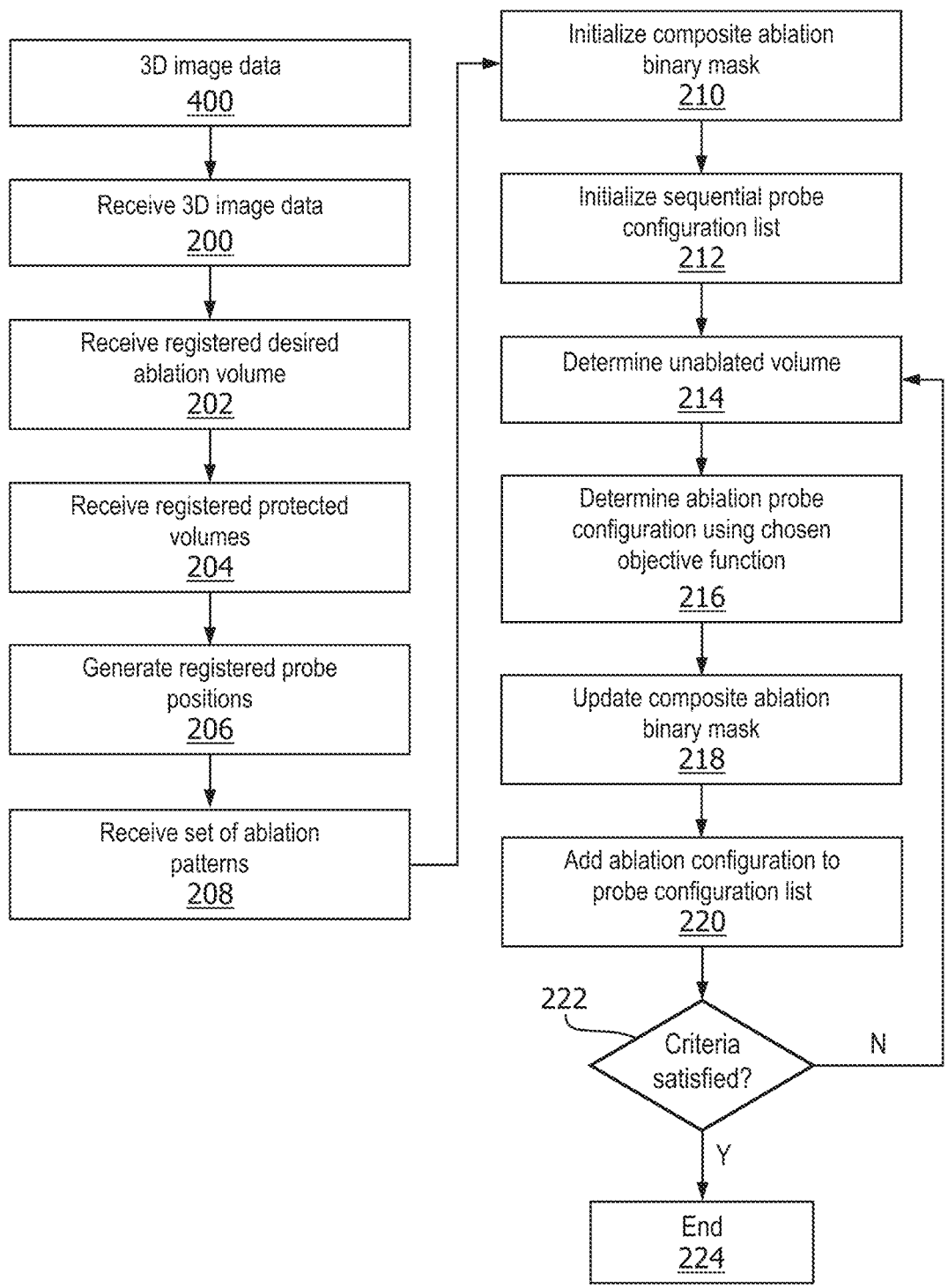
FIG. 4 shows a flow chart which illustrates a method of operating the medical system of FIG. 3.

FIG. 4 depicts a further method of operating the medical system 300 of FIG. 3. The method depicted in FIG. 4 is similar to the method depicted in FIG. 2 except the method starts with step 400 where the medical imaging system 302 is controlled to acquire the three-dimensional medical image data 114. In this case the magnetic resonance imaging system is controlled with the pulse sequence commands 330 and this causes the magnetic resonance imaging system 302 to acquire the magnetic resonance imaging data 332. The magnetic resonance imaging data 332 may then be reconstructed into the three-dimensional medical image data 114.

The treatment planning for ablation concerns the optimal placement of the ablation devices, which is often determined based on the tumor position and size, the device manufacturers' specifications, and the physician's experience. Moreover, in order to reduce unwanted damage to nearby healthy tissues the treatment ablated zone it is desirable to conform as much as possible to the tumor contours. Standard thermal ablation treatment procedures commonly require the physician choosing a set of probe positions and a corresponding set of delivery parameters, for instance ablation power and time values from the device manufacturers' specifications. This manual forward planning procedure can be very lengthy, error-prone and sub-optimal.

Examples may provide for a discrete inverse planning optimization or a mixed discrete-continuous inverse planning optimization approach that is applied to solve the thermal treatment planning problem. Hereto, the clinical expert is only asked to provide following inputs: a set of segmented regions of interest (three dimensional medical image data 114 and the one or more protected volumes 118), a set of clinical goals to achieve (desired ablation volume 118), and ablation specifications (discrete set of ablation patterns 130) for the device (ablation probe) to be used. Then, a set covering iterative greedy algorithm is used to find the optimal minimum number of ablation device configurations (i.e. spatial probe tip positions/orientations and other ablation device parameters) that can satisfy as well as possible the provided clinical protocol goals. A greedy algorithm searches for a local minimum. Moreover, an interactive and simple graphical user interface (GUI) is proposed to allow the clinical expert to directly perform a desired set of actions.

Last but not least, examples may be easily deployed for real-time positioning guidance and adaptive thermal ablation optimization. In the case of detected probe tip misplacements with respect to the exact planned positions, these tracked misplacements can be taken into account to adaptively re-optimize the remaining set (sequential ablation probe configuration list 124) of non-delivered in order to re-establish the expected plan quality.

Examples may be useful for percutaneous ablation cancer treatments. One potential goal of thermal ablation therapy planning is to determine the ablation probe positions and power profiles over time which yield an optimal ablation distribution satisfying the clinical protocol goals (e.g., a certain thermal dose distribution must be delivered to the tumor, sparing as much as possible nearby organs at risk (OARs) (the one or more protected volumes 118). To implement thermal ablation therapy safely and efficiently, it is beneficial to understand the characteristics and limitations of each associated ingredient of the procedure. Given an initial pre-implant CT (computed tomography) or US (ultra sound) image of the patient, the gross tumor volume (GTV) and all nearby normal tissues and organs at risk are manually or automatically delineated. Subsequently, a limited number of probes are virtually inserted inside and/or around the GTV area. Finally, the corresponding optimal power profiles over time are computed producing a wished ablation zone encompassing the tumor. Based on the inflicted organ, size, and location of the tumor the ablation modality—Radiofrequency (RF), Focused Ultrasound (FU), Microwave (MW), Laser, Cryo-ablation—is chosen by the physician. The method for the insertion of the ablation probe into the tumor depends on the inflicted organ, but usually involves free hand device placement.

The treatment planning concerns the placement and operation of the device, which is often determined based on the device manufacturers' specifications, and the physician's experience. In particular, the power control of the device is typically controlled automatically by the ablation device, or manually chosen based on the device manufacturers' specifications.

Figure 5:
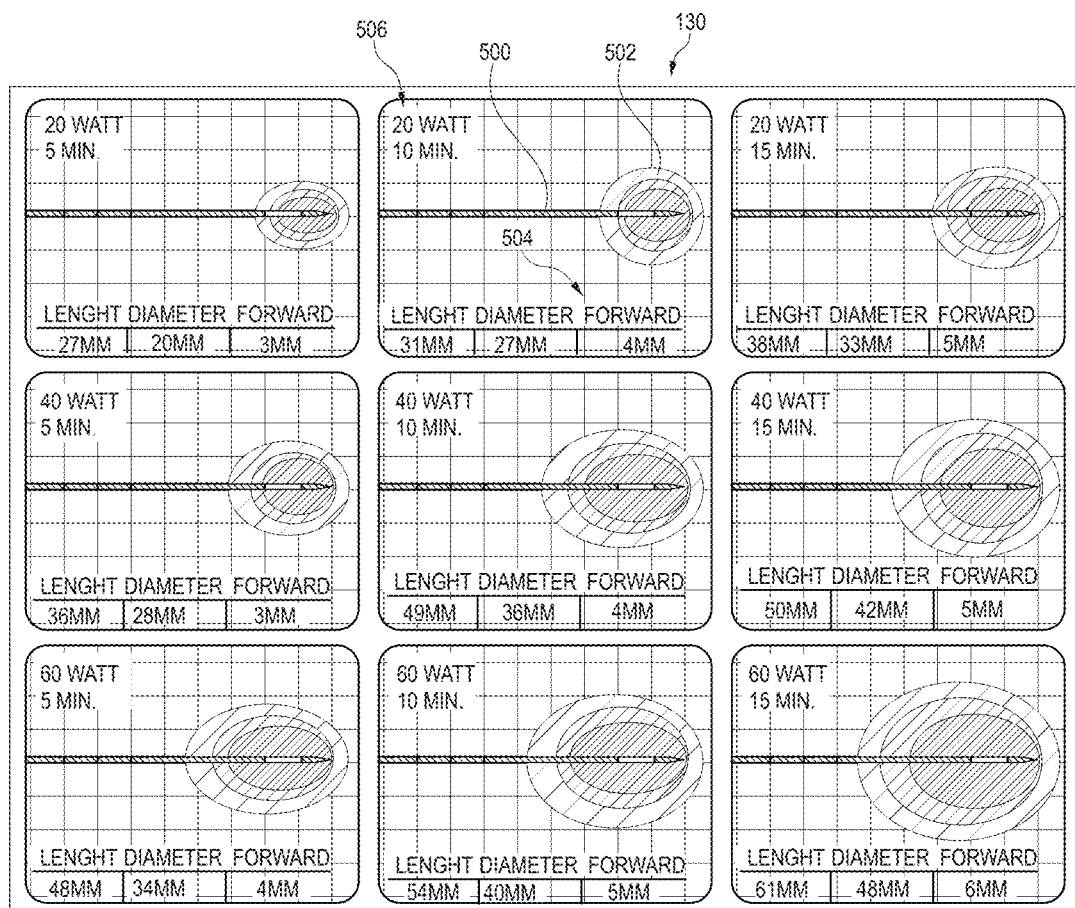
FIG. 5 illustrates an example of a discrete set of ablation patterns.

FIG. 5 illustrates a discrete set of ablation patterns 130. Each of the set comprise an ablation probe 500 and an ablation pattern 502. It may also contain data descriptive of the probe 504 and the particular operating conditions 506 for the individual pattern.

In FIG. 5, a set of "expected" ablation zones are provided for different combinations of the microwave probe ablation power and delivery time settings. Commonly, the manufacturers estimate the ablation size with finite-element analysis using models of heating in tissue. In practice, the size and shape of a single ablation created by a specific electrode could differ and depend upon the tumor's environment, micro-perfusion within the tissue, proximity of the ablation to large blood vessels etc.

In order to ablate an identified tumor area, standard thermal ablation treatment procedures have the physician choosing a set of probe positions and corresponding ablation power and delivery time values from a set of combinations provided on the device supplier datasheet (FIG. 5). In order to reduce unwanted damages to nearby normal tissues and organs at risk (OAR) the ablation zone should be kept as much as possible encompassed within a distance of 1-2 cm from the gross tumor contours. A manual forward planning procedure can be very lengthy, error-prone and sub-optimal since it doesn't employ any numerical optimization methodology to ensure that the best set of ablation device configurations was selected and used for the patient treatment.

From a theoretical perspective, the thermal ablation coverage problem lies in the field of the well-known set covering problems. The best problem solution should present the minimum number of ablations to completely cover the tumor while simultaneously minimizing collateral damage to nearby healthy tissues. Though, set covering problems are NP-hard, accurate solutions can be achieved using a greedy algorithm for polynomial time approximation of set covering that chooses sets according to one rule: "at each stage, choose the set that contains the largest number of uncovered elements".

Figure 6:
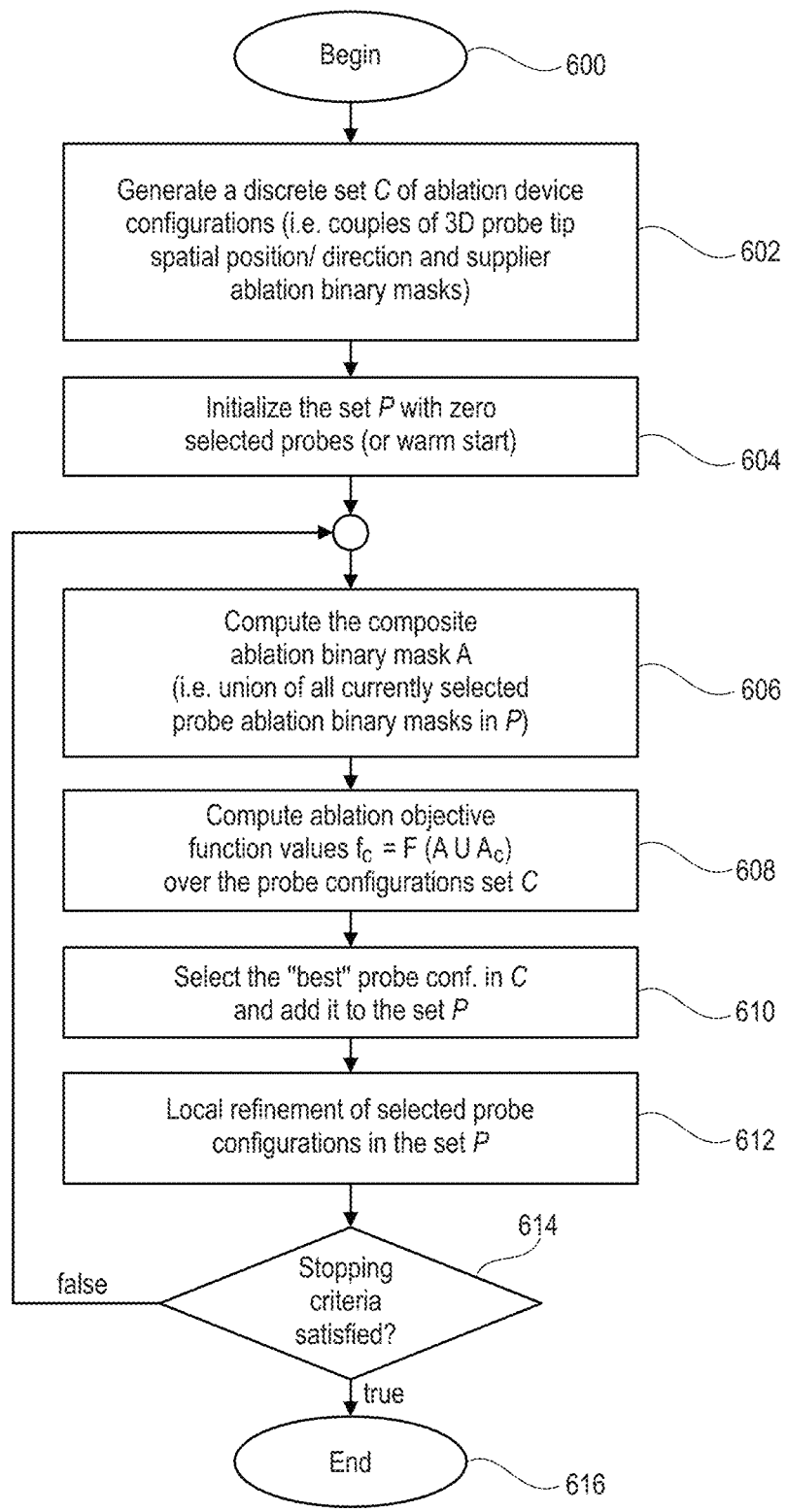
FIG. 6 shows a flow chart which illustrates a further example of a method.

FIG. 6 illustrates an example of a further method. The method begins in step 600. Next in step 602 a discrete set of ablation device configurations is generated. This may include various 3D spatial tip position and direction and also may include the ablation patterns. Next in step 604 the set P is initialized with zero selected probes or selected for a warm start or previous ablation. The method then proceeds to step 606 where the composite ablation binary mask is computed. This is the union of all currently selected probe ablation binary masks in the set P. Next in step 608 the ablation objective function is computed. Then in step 610 the best probe configuration Z is selected and then added to the set P.

Step 612 is optional in some examples. In step 612 the local refinement of the selected probe configuration is performed for step P. This for example may be achieved by changing the discrete locations into various positions which may be varied continuously. The method then proceeds to step 614. Step 614 is a question box; has the stopping criteria been satisfied. If this is true the method proceeds to step 616. If it is false the method then proceeds back to step 606 and more ablation probes and ablation patterns are selected.

Application of the example may comprise one or more of the following 5 steps starting with step 0:

0. The planner takes care to provide a set of segmented regions of interest. This process may be done automatically or based on user input. The segmentation into cancerous, risk, and healthy tissue is of interest. The planner will also take care to translate a prescribed clinical protocol (i.e., a list of prescribed clinical goals/constraints) to corresponding ablation-based mathematical objective functions (e.g., convex quadratic functions) which will be optimized during the subsequent optimization steps. Given the ablation device supplier data, corresponding ablation binary masks are generated for all power-time settings provided in the device datasheet. Here, 1's indicates ablated areas, and 0's non-ablated regions. A 3D grid of potential ablation probe tip positions and probe orientations are sampled. Finally, a discrete set of ablation device configurations is generated by combining the set of sampled 3D probe tip positions/directions with all supplier data-based ablation binary masks related to all possible power-time settings.
1. The current best probe configuration that minimizes the ablation-based objective function value is selected from the discrete set generated at step (0).
2. Given a new set of selected probe configurations at step (1), the corresponding probes' positions are locally refined along with the corresponding ablation binary masks. As previously done at step (1), here an ablation-based objective function is used to guide the optimizer towards the optimal set of probes' tip positions, orientations and delivered ablation binary masks.
3. Steps (1) and (2) are executed repeatedly until a solution satisfying all clinical constraints is reached, and/or the user-defined maximum number of probes was selected.
4. The plan is delivered. Here, new implanted probes could be tracked in real-time. In the case of tracked misplacements compared to the exact planned positions, then steps (1)-(3) are iteratively re-executed until a new re-optimized solution is found.

Another aspect to examples is the optimization problem definition is described in the steps below starting with step 0.

0. Optimization Problem Definition:

The tissue volume under consideration is segmented into structures and binary masks $S_k$ are provided for each k-th structure of interest (i.e. tumor, organs at risk, normal tissue, etc.).

The physician prescribes a clinical protocol with a list of all ablation coverage-based goals that need to be satisfied. A typical goal in thermal ablation therapy is the delivery of conformed ablation over locally cancer cells while sparing as much as possible all nearby healthy tissues. This goal is challenging because ablation of large target volumes conflicts with normal tissue ablation-induced damage tolerance.

Before introducing a set of ablation coverage-based objective functions, a mathematical representation is needed for the delivered ablation zone of a single probe configuration, and for the composite ablation produced by the delivery of multiple probe configurations.

a. Generation of the Initial Discrete Set of Ablation Probe Configurations

Given a supplier device datasheet, the expected ablation zone for each j-th combination of ablation power and delivery time values is converted to a corresponding 3D ablation binary mask:

$$A_j(x) = \begin{cases} 1 & \text{if the position } x \text{ is inside the expected ablated zone} \\ 0 & \text{otherwise} \end{cases} \quad (E1)$$

Figure 7:
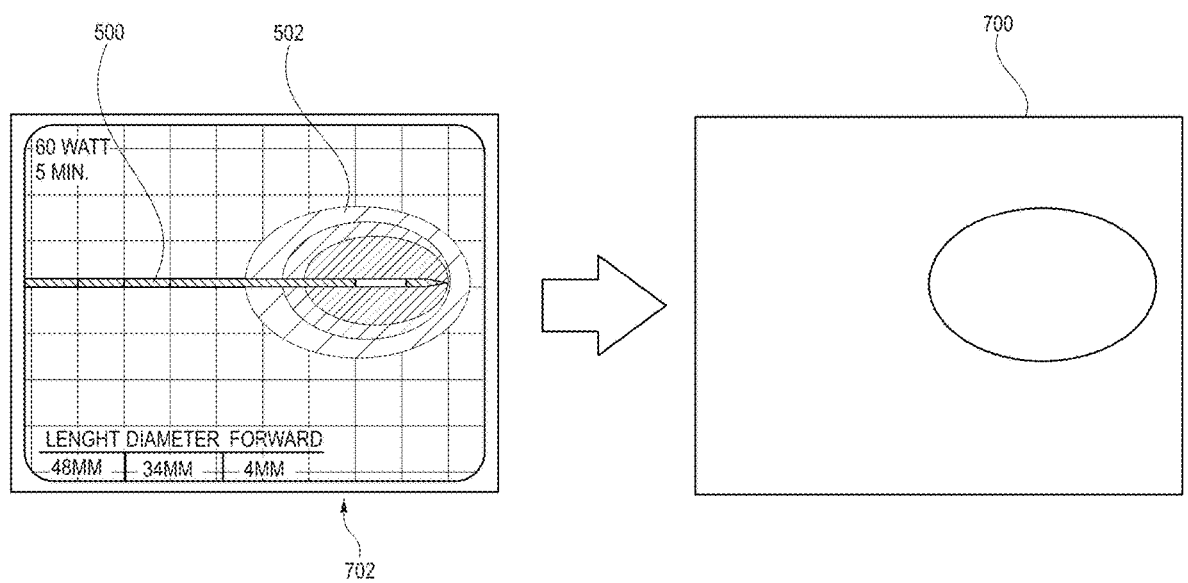
FIG. 7 illustrates an example of creating an ablation binary mask.

FIG. 7 illustrates how an ablation device configuration 702 which comprises a specification of an ablation probe and an ablation pattern 502 is used to generate an ablation mask 700. It can be seen that the region of the ablation pattern 502 is selected to make the mask 700. The ablation device configuration uses (power,time)=(60 W, 5 min) and the corresponding ablation binary mask (right, Equ. E1) for the microwave ablation device.

In this invention, a discrete set C of $N_c$ probe configurations is built. Here, each probe configuration consists of a combination of discretized probe paths (i.e. skin insertion point, direction and final probe tip position), and the expected binary mask $A_c$ produced by a power-delivery time setting (FIG. 3, right). In order to keep a moderately low cardinality for the set C, only probe configurations with binary masks at least partly overlapping the tumor region will be considered. Moreover, thanks to a subsequent local refinement of the discrete positions and directions of the best selected probes, a moderate sampling factor and a coarse spatial discretization of the probe positions and directions can be used to populate the set C.

Finally, when multiple ablation device configurations are delivered, the composite ablation binary mask A is defined as the union of all related ablation binary masks $A_s$:

$$A = \cup_s A_s \quad (E2)$$

b. The Ablated Fractional Structure Volume

Figure 8:
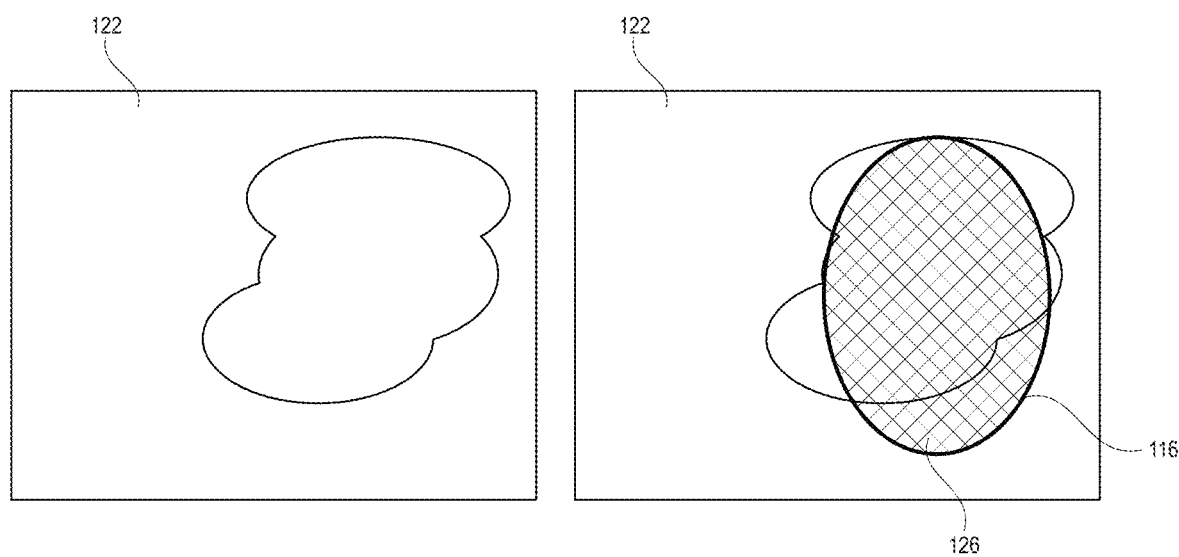
FIG. 8 illustrates a composite ablation binary mask.

The notion of ablated fractional volume is used in the following for quantifying the amount the volume of a structure that is affected by ablation. Given a k-th segmented structure, its currently ablated fractional structure volume $v_k$ produced by a composite ablation binary mask A is given by:

$$v_k(A, S_k) = 100 \cdot \frac{|A \cap S_k|}{|S_k|} \quad (E3)$$

here $S_k$ indicates the binary mask of the k-th segmented region of interest, $|\cdot|$ is the cardinality (i.e. the size) operator, and $|A \cap S_k|$ indicates the cardinality of the intersection between the cumulative ablated volume and the structure (i.e. the portion of segmented structure which is currently ablated, see FIG. 8).

FIG. 8 illustrates two views of a composite ablation binary mask 122 made from three different ablations. On the left is the composite ablation binary mask by itself. On the right shows the composite ablation binary mask 122 with the desired ablation volume 116. The region marked 126 is the unablated volume.

c. The Thermal Ablation Composite Objective Function

Generally, clinical goals for all regions of interest are translated into corresponding two- or one-sided closed proper ablation coverage-based functions of class $C^2$ $f_1(A), \ldots, f_m(A):\Omega \to \mathbb{R}$ In order to achieve a required ablation coverage of the tumour while sparing as much as possible nearby healthy tissues, the physician could prescribe thresholds for ablation coverage in all regions of interest, e.g. a given minimum (and/or maximum) volume fraction t of a k-th structure is ablated. For this purpose, the following quadratic ablation coverage-based objective functions might be used as optimization constraints:

$$f^{min}(A) = H(t - v_k(A, S_k))\left(\frac{t - v_k(A, S_k)}{t}\right)^2 \quad (E4)$$

$$f^{max}(A) = H(v_k(A, S_k) - t)\left(\frac{t - v_k(A, S_k)}{t}\right)^2 \quad (E5)$$

here $H(\cdot)$ is the Heaviside step function, t is the prescribed minimum (maximum) ablation fractional volume threshold, and $v_k$ indicates the current ablated fractional structure volume produced by the composite ablation A (see Equ. E3).

All mathematical objectives $f_i(A)$ are given as functions of the composite ablation zone binary mask A produced by all selected ablation probe configurations (Equ. E2).

The following composite objective function $$F(A) = \sum_{i=1}^{m} w_i f_i(A) + w_R R(A) \quad (E6)$$

can be defined and minimized to achieve the wished ablation coverage.

The quantities $w_i$ and $w_R$ represent manually set importance weights for all ablation coverage-based objective functions and a regularization term, respectively.

The regularization term R(A) is optional, and might have different forms. This can be used to enforce some requested specific ablation zone characteristics. For example, we could use a Tikhonov regularization to avoid a too high cardinality (i.e size) for the composite ablation binary mask A, or a regularization term to control (e.g. reduce) the size of the overlaps (i.e. intersections) among all delivered probes' ablation binary masks leading to redundant ablations of tumor sub-regions.

1. Optimal Discrete Probe Configuration Selection:

In this invention, we assume that a discrete set C of $N_c$ probe configurations is given, and for each configuration c-th an ablation binary mask $A_c$ has been computed (step 0).

P is defined as the set of currently selected probes configurations, and A its corresponding composite (i.e. union) ablation zone binary mask computed as indicated in Equ. E2.

A goal for some examples that use set covering greedy iterative algorithm is to add to the selection set P a new probe configuration c* which can potentially lead to an improved value of the ablation-based function F(A) at Equ. (E6).

For the selection of the best probe configuration, at current step n, an objective function value $f_c$ is computed for each possible c-th probe configuration by:

$$f_c = F(A \cup A_c), c=1, \ldots, N_c. \quad (E7)$$

Here, c represents the index of the ablation probe configuration, and Nc is the total number of probes' configurations in the discrete set C.

At each iteration n, the probe configuration c* corresponding to the minimum objective function value is selected and added to the optimal set P of probe configurations:

$$c = \min\{f_c\}, c=1, \ldots, N_c. \quad (E8)$$

a. Speeding-Up the Ablation Composite Objective Function Evaluation

In this example a greedy iterative algorithm is disclosed where a number of optimal probe configurations are progressively selected. The selection of the best probe configuration requires to compute the functional objective $f_c = F(A \cup A_c)$ for all $N_c$ ablation device configurations at each algorithm iterate.

As a consequence, all ablated fractional structure volumes $v_k$ (Equ. E3) are recomputed at each algorithm n-th iteration for all $N_c$ ablation device configurations.

These volumetric computations can represent a serious bottleneck for the algorithm performances.

In order to speed-up these computations the following equation can be used:

$$v_k(A \cup A_c, S_k) = v_k(A, S_k) + v_k(A_c, S_k) - v_k(A \cap A_c, S_k). \quad (E9)$$

Here, on the right size of the Equ. E9, the $v_k(A, S_k)$ quantities can be precomputed at beginning, the $v_k(A, S_k)$ values are given and known from the previous algorithm iteration, while only the final term $v_k(A \cap A_c, S_k)$ may be computed to get the new $v_k(A \cup A_c, S_k)$ value for all $N_c$ ablation device configurations.

Since the cardinality of the intersection set $(A \cap A_c)$ is obviously smaller than the cardinality of the union set $(A \cup A_c)$, computing $v_k(A \cup A_c, S_k)$ using the Equ. 9 can drop enormously the required computation time.

2. Iterative Local Refinement of the Selected Probe Configurations:

Given a new set P of selected probe configurations from step (1), the corresponding probes' spatial positioning and delivered ablation binary mask can be locally refined by solving a mixed discrete-continuous iterative constrained optimization problem.

This local refinement step is not mandatory, and could be dropped when the spatial discretization used for the generation of the initial set C of probe configurations at step (0) is considered accurate enough by the physician.

However, if a very coarse spatial discretization is used to reduce the computational burden of step (1), an iterative local refinement step can be performed to improve the precision of the delivered probe configurations and consequently to increase the ablation coverage of the tumor (see FIG. 9 below).

At each refinement iteration, firstly, the optimal local rigid transformations of all currently selected probes' ablation masks are determined by minimizing an ablation-based functional related to the treatment goals.

Figure 9:
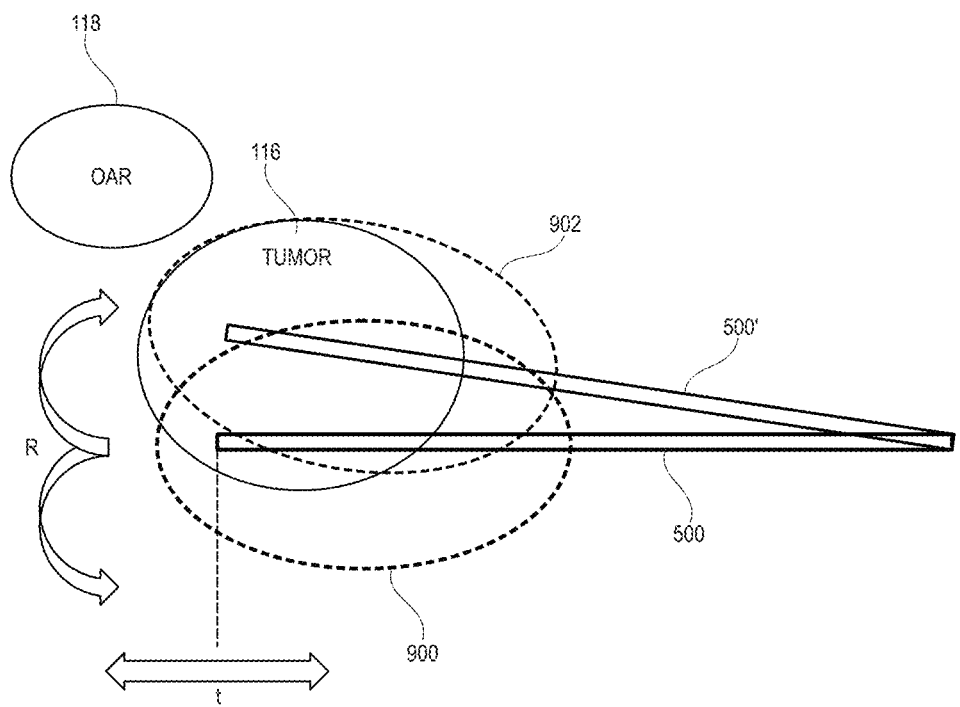
FIG. 9 illustrates the local refinement of an ablation probe position and/or orientation.

FIG. 9 illustrates a repositioning of the ablation probe. 500 indicates the position. The position can be varied via a rigid transformation into position 500'. The new adjusted ablation position is 902. This has much better coverage of the desired ablation volume 116 and still avoids the protected volume 118. FIG. 9 illustrates a local refinement of a probe position/orientation and its ablation zone binary mask by rigid transformation. Starting from an initially selected discrete probe position and ablation binary mask, an optimal roto-translation transformation (R, t) is computed and applied to the probe position/direction in order to increase the ablation coverage of the tumor.

This can be achieved by minimizing the function introduced at Equ. E6

$$F(R_p,t_p)=F(A[R_p,t_p])=\Sigma_{i=1}^{m}w_if_i(A[R_p,t_p])+w_RR(A[R_p,t_p]) \quad (E10)$$

with respect to the parameters of rigid transformations $R_p, t_p$ used to transform the selected probe tip positions and directions and associated binary masks at each grid position x:

$$A[R_p,t_p](x)=\cup_{p\in P}A_p(R_px+t_p) \quad (E11)$$

Optionally, lower and upper bounds could be enforced to the optimization problem in order to limit the optimization search to the feasible solution set containing only roto-translation transformations of the probes that are clinically deliverable.

Finally, as a result, optimal rigid transformation parameters ($R_p^*$, $t_p^*$) for all selected probe configurations are obtained.

As a second local refinement step, the rigidly transformed probes' positions are kept fixed and the corresponding delivered ablation binary masks $A_p$ are optimally updated. Here, all possible binary masks provided in the device manufacturers' specification are evaluated at current roto-translated probes' positions. Finally, the new set of ablation masks $A_p$ is selected that produces the minimum ablation-coverage objective functional value (see FIG. 10 below).

Figure 10:
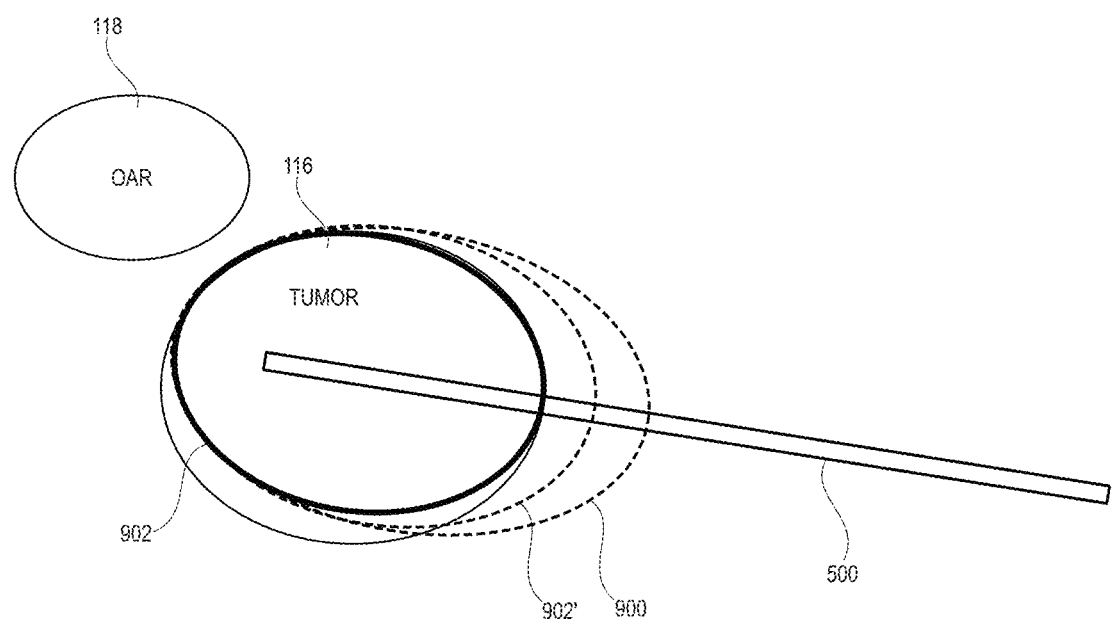
FIG. 10 illustrates a local refinement of a ablation zone for an ablation probe.

FIG. 10 illustrates a probe ablation mask optimization. In this example the initial position of the ablation probe 500 is varied so that the initial position 900 is moved into a number of different adjusted ablation positions 902, 902'. In this case the position 902 better covers the desired ablation volume 116 and still avoids the one or more protected volumes 118. All possible ablation binary masks from the manufacturer's specifications may be evaluated at current optimal roto-translated probes' positions. Then, the ablation binary masks producing the best objective functional value are selected.

To reduce the computational cost of this local refinement step, we could limit the objective function evaluations to only update the ablation binary mask of the very last selected probe configuration at step (1), while the binary masks of all other selected probes are kept fixed.

This iterative local refinement step will toggle between the probe's positioning optimization and the optimal binary masks selection till a user-prescribed ablation-based objective functional precision, and/or a maximum number of local refinement iterations, is achieved.

3. Iterative Optimization Strategy:

The procedure parameters (P, t) are optimized in an iterative strategy that toggles between an optimal selection of probe configurations out of a initial discrete set (step 1), and a local refinement of the currently selected probe configurations (step 2) using continuous optimization methods.

A flow chart of the proposed greedy iterative method is given at FIG. 6. Firstly, during the step (1), the best probe configuration is selected out of a big set of discrete probe configurations, then, during the second step, all currently selected probes are locally repositioned to improve the total ablation coverage of the tumor, and so on.

The algorithm iterations will be stopped if/when a given relative ablation coverage-based functional F precision is achieved, and/or a given maximum number of selected ablation probe was reached. In these cases, the last achieved solution with $N_{sol}$ selected probes is returned.

Finally, to improve the total computation time, one could select more than one new probe configuration at each iteration. This will reduce the number of function computations needed to find the best solution to the expense of some degradations in terms of ablation coverage quality.

The set of selected probes' configurations P and the corresponding composite ablation zone A can be properly initialized by exploiting the clinical expert's a-priori knowledge.

If no such initialization is available a completely empty initial setting (i.e. P=Ø, A=Ø) is assumed; then this iterative strategy will populate the P set with most promising probe configurations.

4. Real-time orientation guidance and adaptive ablation coverage optimization:

The plan optimized at step 3 can be delivered by clinical experts. Here, implanted probes are continuously tracked in real-time. In the case of detected probe tip misplacements with respect to the planned positions, these tracked misplacements can be taken into account to adaptively re-optimize the remaining set of probes and the corresponding composite ablation (steps (1)-(3)) in order to re-establish the expected plan quality.

Figure 11:
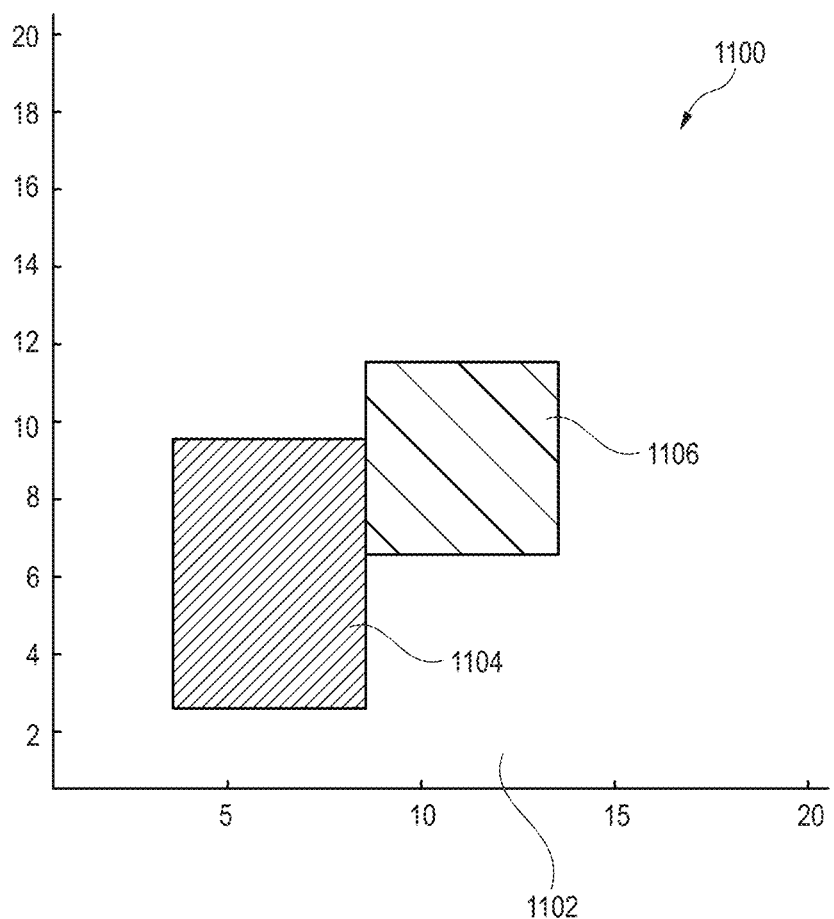
FIG. 11 illustrates synthetic phantoms used for a numerical simulation of an ablation.

FIG. 11-21 illustrate an example that was evaluated using synthetic data. A 3D synthetic phantom was used consisting of a tumor volume 1104, an organ at risk (OAR) region 1106, and a healthy tissue area 1102. Hereto, a 3D isotropic grid with 20 voxels per direction was used where the target region (FIG. 11, 1104) is a parallelepiped of sizes 7×5×5 voxels, the OAR region (FIG. 11, 1106) is a cube of edge of 5 voxels, and the remaining 3D grid is segmented as normal tissue region (FIG. 11, 1102).

As mentioned above, FIG. 11 illustrates a synthetic phantom 1100 which is used for a simulation of a method. Within the synthetic system the large area marked 1102 represents normal tissue. The region indicated by 1104 indicates a tumor or a desired ablation volume. The volume labeled 1106 represents an OAR or organ at risk which is equivalent to the protected volume.

An initial discrete set C of ablation device configurations was generated before starting the iterative optimization method. A simulated ablating probe delivering spherical ablation zones with radii of 0.5, 1 and 2 voxels was used for the experiments. For the probe tip spatial positions and orientation, only probe configurations with spherical binary masks at least partially overlapping with the tumor region were considered. Finally, a total of $N_C$=3513 probe configurations were pre-computed as an input for the algorithm. The prescribed optimization protocol and the corresponding mathematical objectives are shown in Table I. In this experiment, no regularization was added to the composite ablation-based objective functional. Finally, a maximum number of 15 ablation probes, and a relative objective functional precision of 1E-15 were used as stopping criteria.

Figure 12:
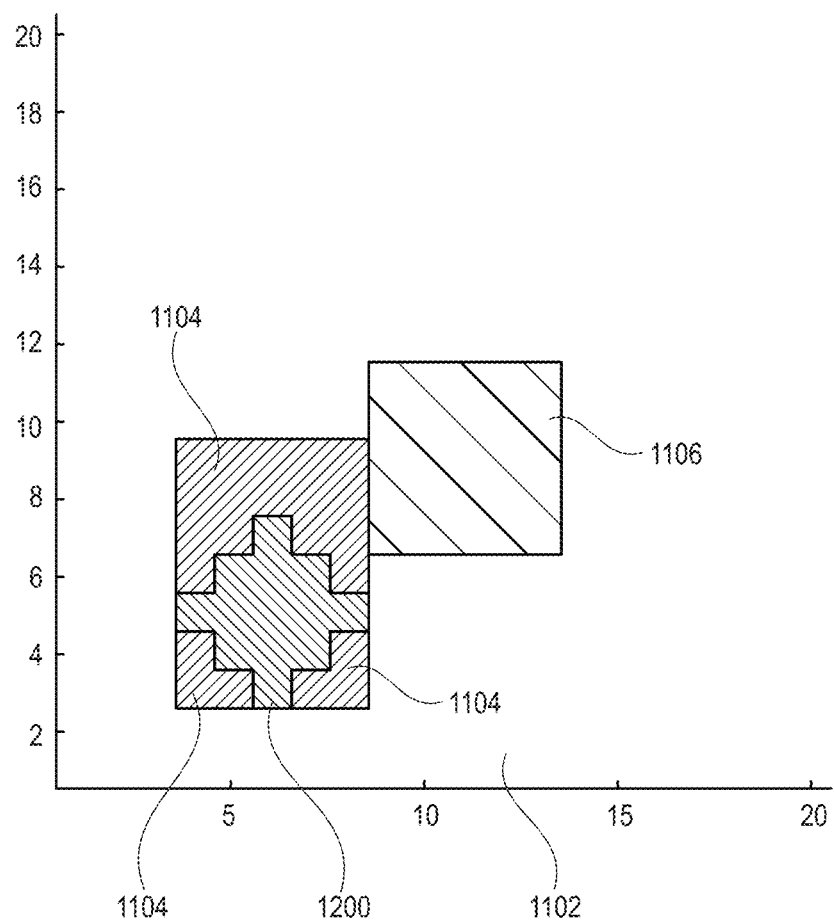
FIG. 12 illustrate a simulation of using one ablation probe for the synthetic phantoms of FIG. 11.

After 12 iterations, the best set of 12 probe configurations fully satisfying all prescribed protocol constraints was returned. The optimal objective functional values at each iteration are given in Table II. The ablated regions (blue color) at different iterations are shown in FIG. 12. The ablation composite objective functional values at each iteration are plotted in FIG. 13. Finally, the ablated fractional volumes for the tumor, the OAR and the normal tissue regions are shown on FIGS. 14, 15 and 16, respectively.

FIG. 12 shows the simulation after ablation with one probe. The region 1200 represents the ablation zone 1200. The single ablation has only ablated a portion of the tumor 1104.

Figure 13:
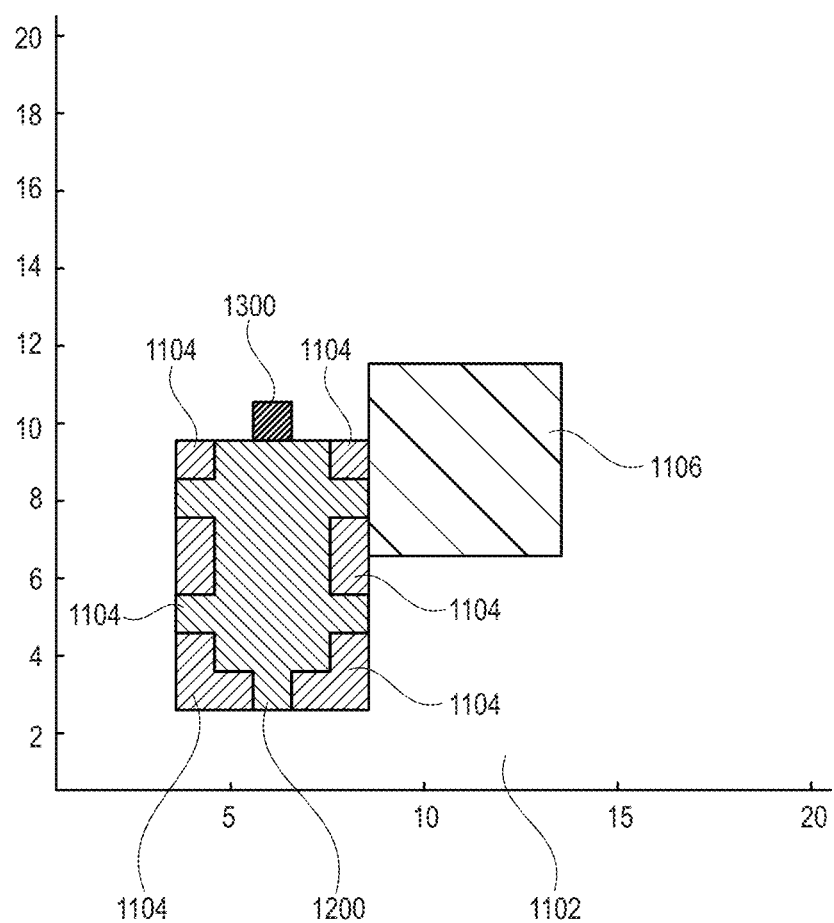
FIG. 13 illustrate a simulation of using two ablation probes for the synthetic phantoms of FIG. 11.

FIG. 13 shows the simulation after ablation with two probes. The ablated zone 1200 has grown. The region marked 1300 is the ablation zone in the normal tissue 1102.

Figure 14:
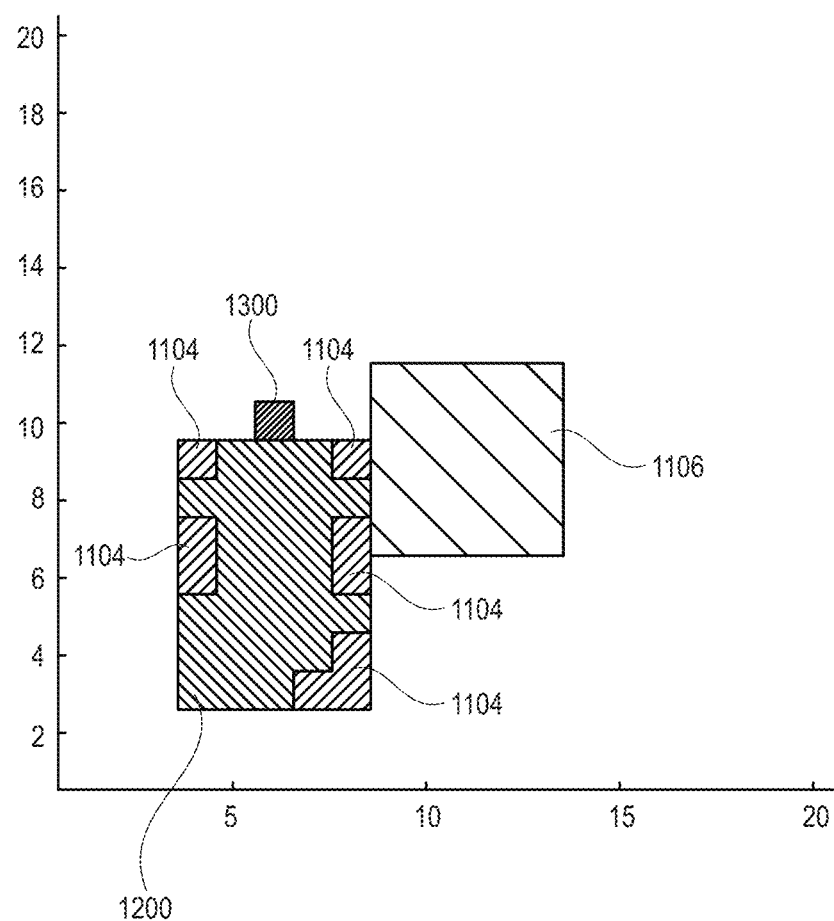
FIG. 14 illustrate a simulation of using three ablation probes for the synthetic phantoms of FIG. 11.

FIG. 14 shows the simulation after ablation with three probes.

Figure 15:
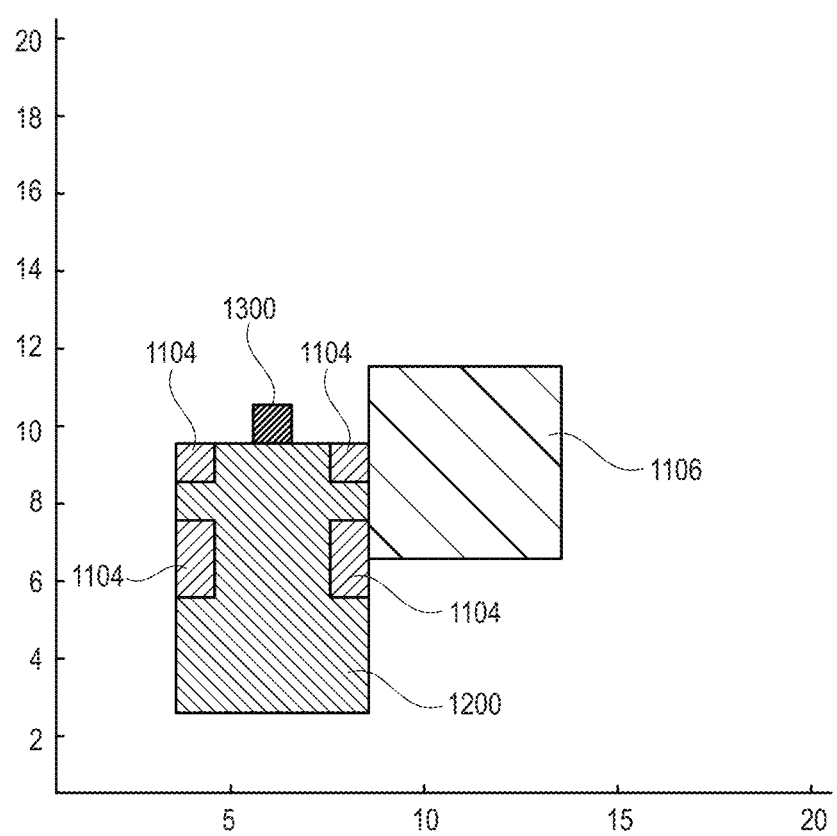
FIG. 15 illustrate a simulation of using four ablation probes for the synthetic phantoms of FIG. 11.

FIG. 15 shows the simulation after ablation with four probes.

Figure 16:
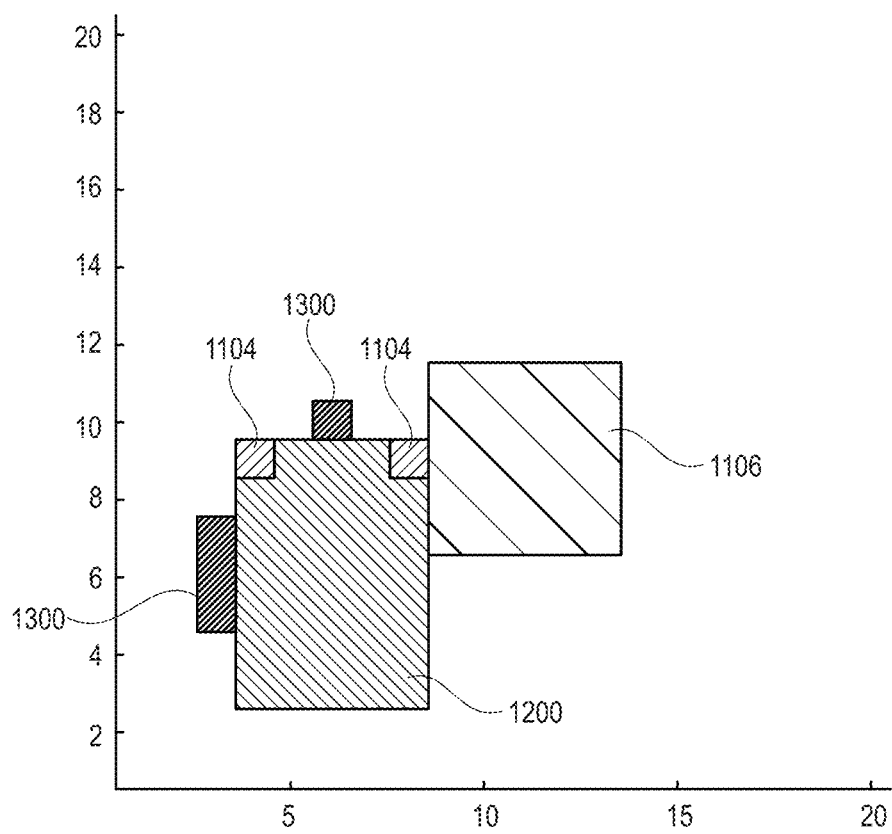
FIG. 16 illustrate a simulation of using seven ablation probes for the synthetic phantoms of FIG. 11.

FIG. 16 shows the simulation after ablation with seven probes.

Figure 17:
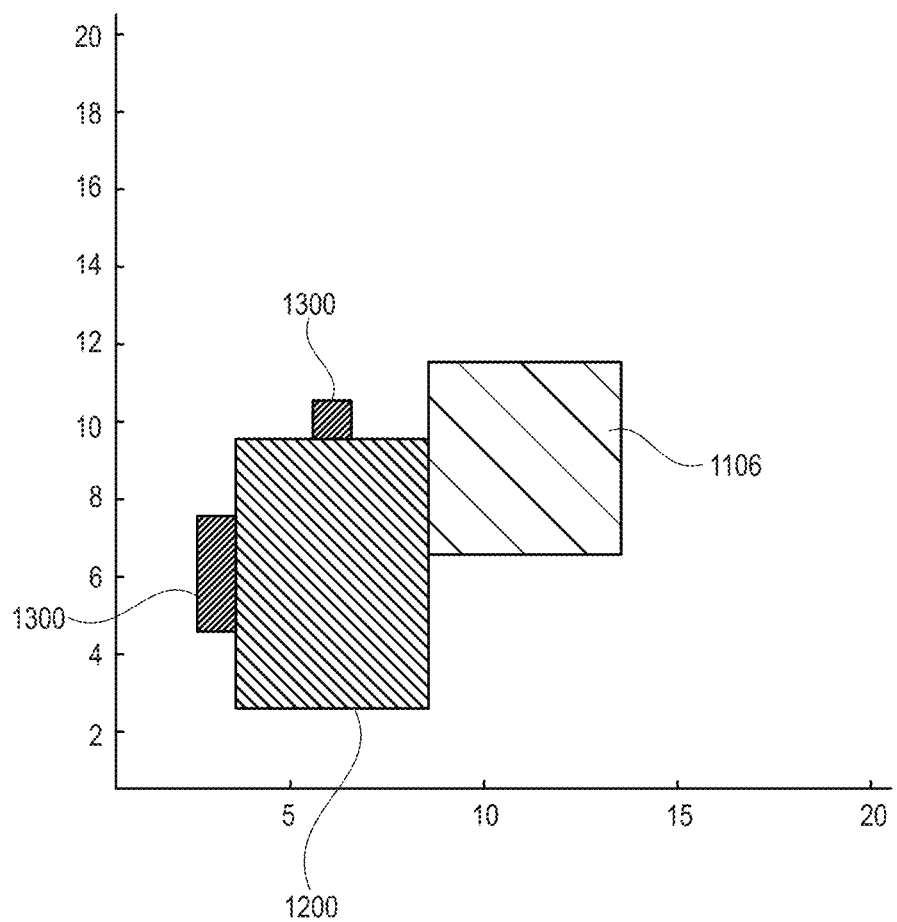
FIG. 17 illustrate a simulation of using twelve ablation probes for the synthetic phantoms of FIG. 11.

FIG. 17 shows the ablation after using 12 probes. Some experimental results are summarized in tables I and II below.

TABLE I

Step 0-Problem definition: clinical protocol and corresponding mathematical objectives.

| Ablation Objective Function | Region [color, see FIG. 7] | Ablation Volume Threshold [%] | Importance Weight |
|---|---|---|---|
| MinVolumeFraction | Tumor [red] | 95 | 1 |
| MaxVolumeFraction | Risk Organ [green] | 2 | 1 |
| MaxVolumeFraction | Healthy Tissue [white] | 1 | 1 |

TABLE II

The ablation functional values, and the fraction of ablated structure volume at each iteration.

| Number of iterations (i.e. probes) | F(A) | $v_{Tumor}(A)$ [%] | $v_{OAR}(A)$ [%] | $v_{NT}(A)$ [%] |
|---|---|---|---|---|
| 0 | 1.0000 | 0.00 | 0.00 | 0.00 |
| 1 | 0.6524 | 18.86 | 0.00 | 0.00 |
| 2 | 0.3857 | 36.00 | 0.00 | 0.01 |
| 3 | 0.2754 | 45.14 | 0.00 | 0.05 |
| 4 | 0.1837 | 54.29 | 0.00 | 0.09 |
| 5 | 0.1186 | 62.29 | 0.00 | 0.23 |
| 6 | 0.0677 | 70.29 | 0.00 | 0.38 |
| 7 | 0.0331 | 77.71 | 0.80 | 0.39 |
| 8 | 0.0134 | 84.00 | 0.80 | 0.43 |
| 9 | 0.0054 | 88.00 | 0.80 | 0.66 |
| 10 | 0.0014 | 91.43 | 0.80 | 0.90 |
| 11 | 2.26E−06 | 94.86 | 1.60 | 0.92 |
| 12 | 0.0000 | 95.43 | 1.60 | 0.92 |

Figure 18:
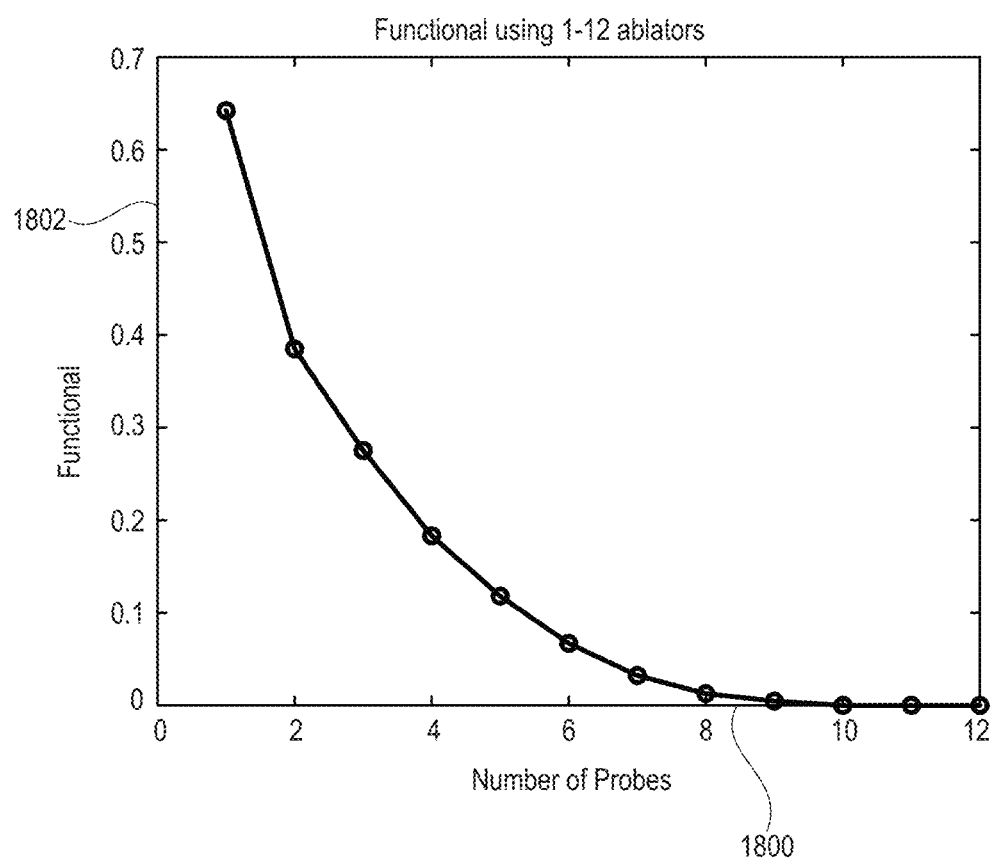
FIG. 18 illustrate the ablation objection function F(A) for different iterations of the simulations illustrated in FIGS. 11 through 17.

FIG. 18 shows the value of the objective function f of a as a function of the number of probes used 1800. This is the ablation objective function F(A) values at each iteration for the simulation illustrated in FIGS. 11-17.

Figure 19:
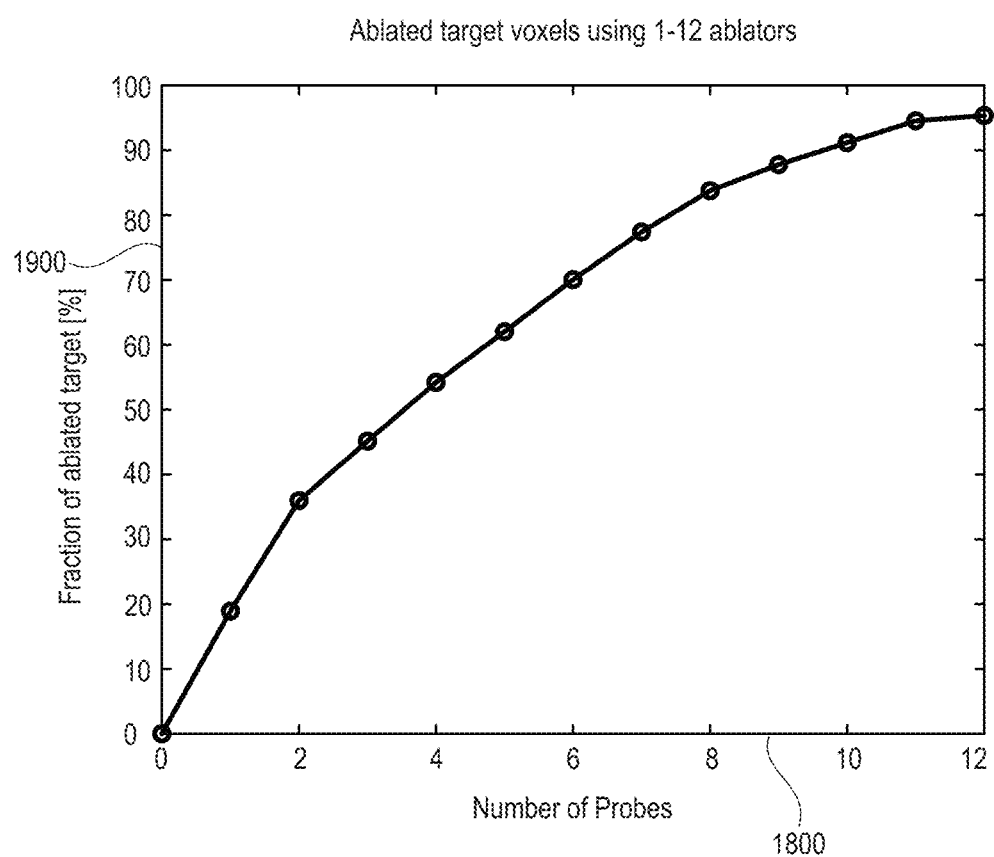
FIG. 19 illustrates the fraction of the ablated target for different iterations of the simulations illustrated in FIGS. 11 through 17.

FIG. 19 shows the fraction of the ablated target 1900 as a function of the number of probes 1800 used. This is the Fraction of ablated target region $v_{Tumor}(A)$.

Figure 20:
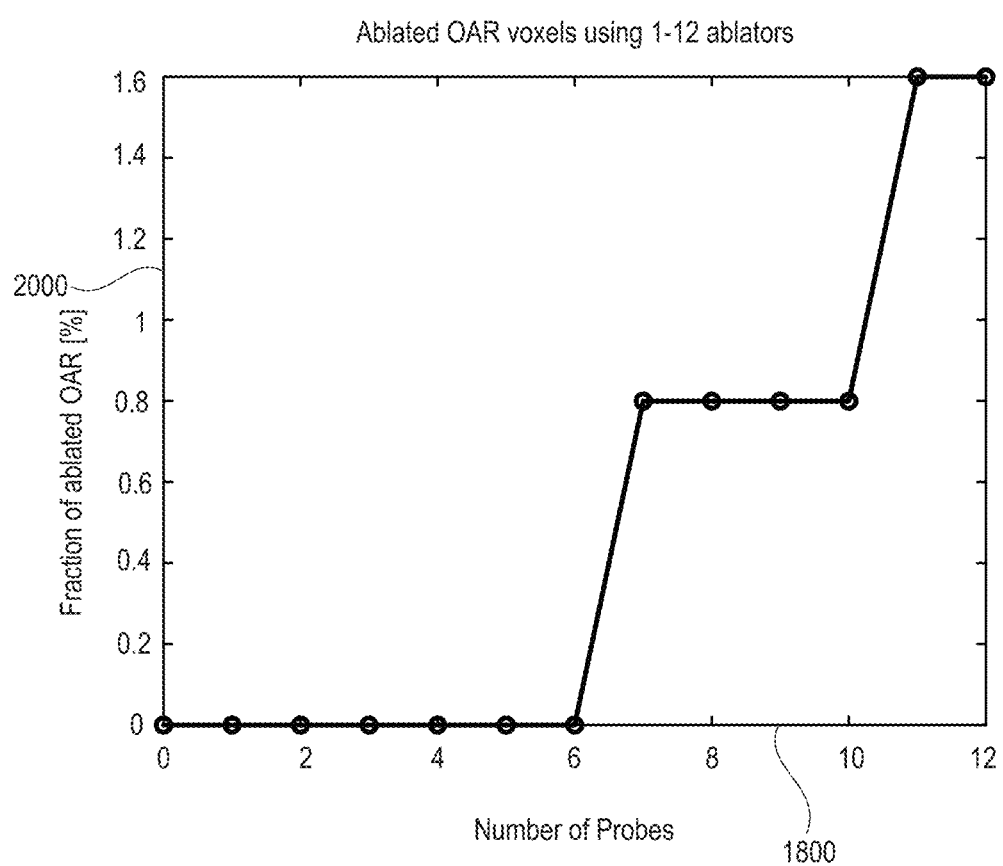
FIG. 20 illustrates the fraction of ablation for the OAR region for different iterations of the simulations illustrated in FIGS. 11 through 17.

FIG. 20 shows a fraction of the ablated OAR region $v_{OAR}(A)$ as a percentage 2000 as a function of the number of probes 1800 used. It can be seen that even after using 12 probes the fraction of the OAR which is ablated does not exceed 1.6%.

Figure 21:
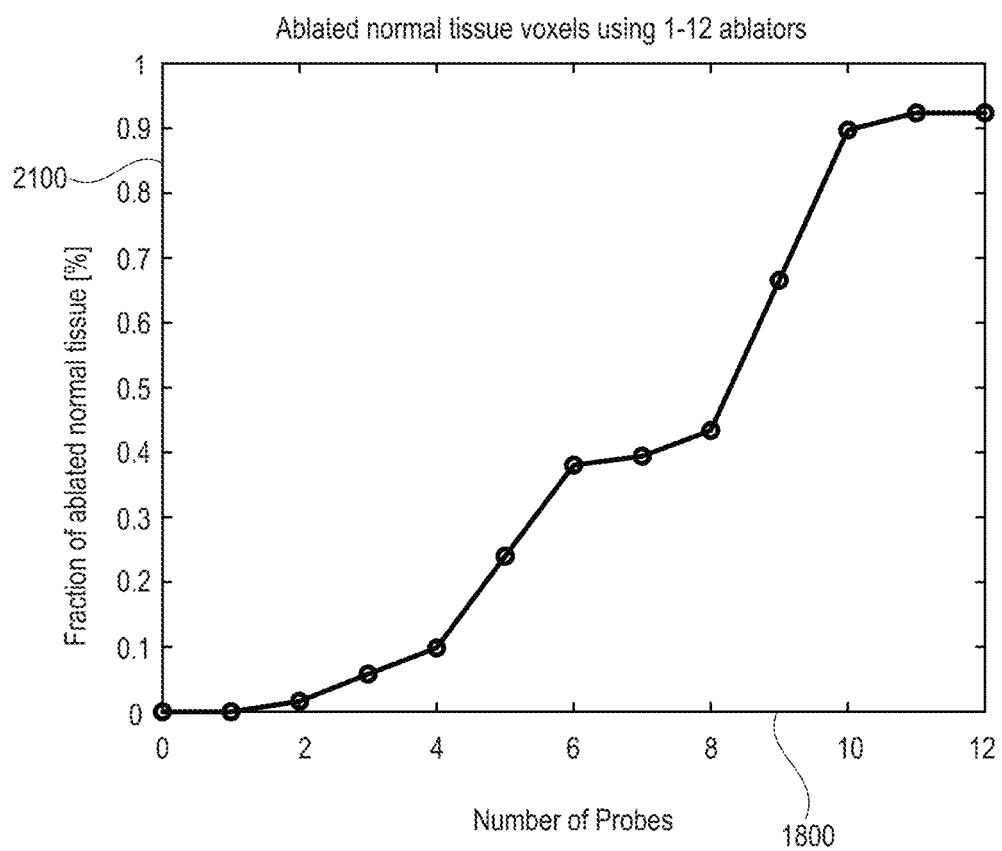
FIG. 21 illustrates the fraction of ablation for the normal tissue for different iterations of the simulations illustrated in FIGS. 11 through 17.

FIG. 21 shows a fraction of ablated normal tissue region A) as a percentage 2100 as a function of the number of probes 1800.

Some examples may also provide for a Thermal Ablation Therapy Planning System GUI.

The user interactions and actions with the user interface may comprise one or more of the following features:

Selecting the ablation device to use for treatment delivery;

Importing diagnostic patient images (e.g. US, CT, MR, etc.);

Segmenting the anatomical structures of interest on a diagnostic image of the patient;

An optional images registration for cancer delineation could be required; Manual (or automatic) selection of a discrete set of potential skin entry points to use for treatment delivery;

Generation of a discrete set of ablation probe configurations;

Prescription of a clinical protocol (i.e. a set of constraints/goals to satisfy);

Inverse planning treatment plan optimization;

Optimal treatment plan delivery execution.

The last two features in the list above could be iterated multiple times if an adaptive real-time treatment planning and delivery workflow is applied (see previous step (4)).

Figure 22:
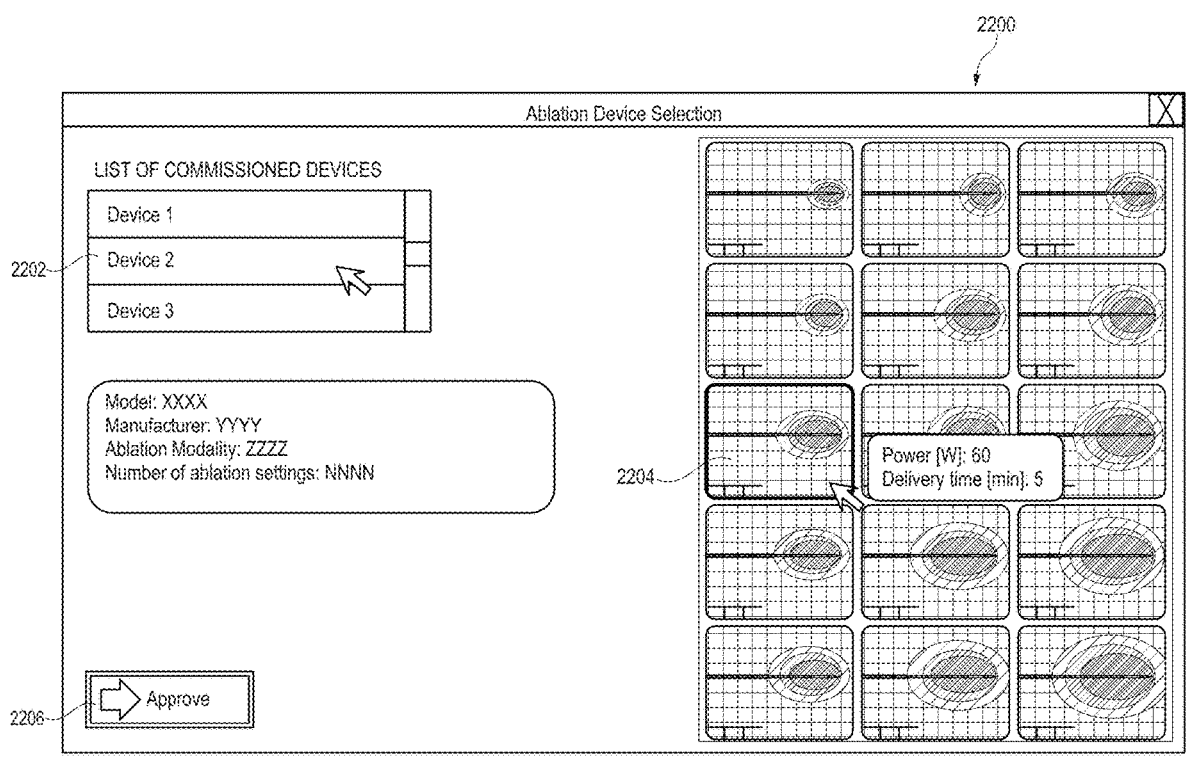
FIG. 22 illustrates an example of a graphical user interface.

In FIG. 22, a example of the GUI tab for the user selection of the ablation device to use is given. Here, the user can select an ablation device from a list of pre-commissioned devices, then manufacturer's data are readily displayed. Finally, the user is asked to approve the selected device.

FIG. 22 illustrates an example of a user interface 2200. This user interface 2200 has a control 2202 to select a list of commissioned probes. This user interface 2200 also has a control 2204 to select a configuration for the probe. This may for example determine a power and delivery time that is used. Ablation patterns may be displayed for the convenience of the operator. The user interface 2200 also contains a control 2206 for approving the selection. Here the user can select an ablation device from a list of pre-commissioned devices. Manufacturer's data may also be readily displayed.

Figure 23:
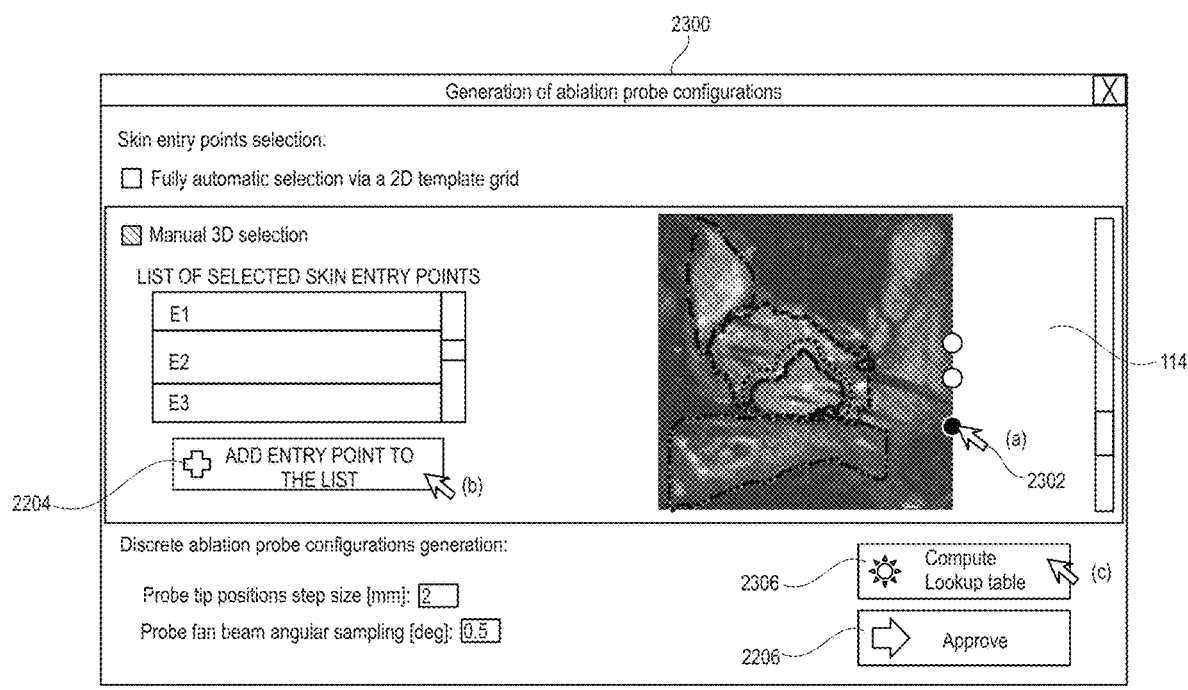
FIG. 23 illustrates a further example of a graphical user interface.

FIG. 23 illustrates a user interface that is used to generate ablation probe configurations. A medical image 114 is displayed as well as possible skin entry points 2302. These for example may be selected manually. The control 2204 enables addition of an entry point to a list. There is a control 2304 which adds entry points by using a look up table. There is a control 2206 to approve the selection. FIG. 23 is useful for the generation of the discrete set of ablation probe configurations (discrete set of ablation probe positions). Here, a number of potential skin entry points E1, E2, E3, . . . is selected (a-b). The list of entry points might be computed also automatically if, as for brachytherapy treatments, a 2D template grid is used for treatment delivery. Finally, a lookup table of probe configurations is computed based on the provided set of skin entry points, a number of user given parameters, and the device supplier data (c).

In FIG. 23, a mock-up of the GUI tab for the generation of the discrete set of ablation probe configurations (see step (0.a)) is shown. Here, a number of potential skin entry points is manually selected (a-b). The set of entry points might be computed also automatically if a 2D template grid is used for treatment delivery. After a list of skin entry points is provided, the user is asked to set a number of discretization parameters, as for instance, the probe fan beam angular sampling which is used to compute the straight trajectories under a set of discrete angles. These probe fan beam trajectories will be computed originating from all provided skin entry points. A step size is also provided to discretize a number of probe tip positions along each straight probe trajectory. The device supplier's ablation data and the tumor segmented binary mask can be used to neglect all probe configurations with no overlap between the expected delivered ablation and the target tumor region.

Figure 24:
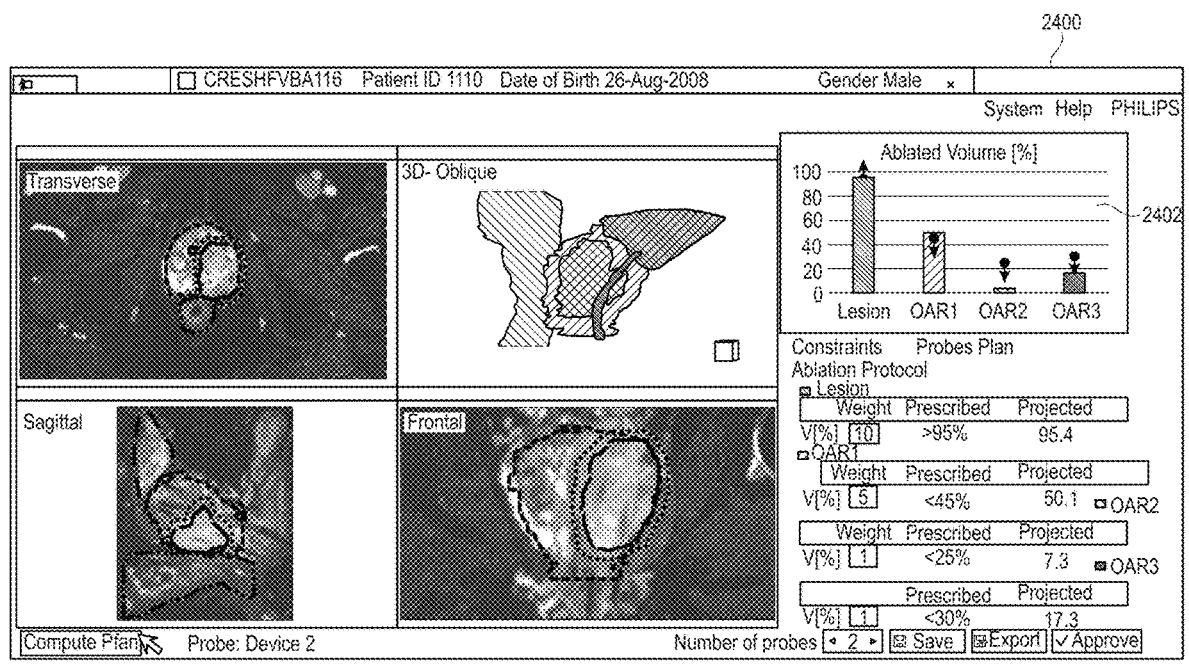
FIG. 24 illustrates a further example of a graphical user interface.

FIG. 24 illustrates a further user interface 2400 which is a thermal ablation inverse planning tab. There is a chart 2402 which illustrates the ablated volumes for the lesion, and several organs at risk. In FIG. 24, the thermal ablation inverse planning tab is presented. Here, transverse, sagittal, frontal and 3D rendered images of the patient are given. Segmented structures may be, for example, delineated with different colors. The optimal total ablated region is visualized and superimposed over the patient image. To facilitate the plan evaluation, a plot of the ablated structures' volume fractions at current optimized plan may be given. Here, for example, a colored column bars plot can be used to show the current ablated portion of structure volume. In this plot, up/down oriented arrows can be used to indicate the minimum/maximum ablated volume thresholds prescribed in the clinical protocol. Finally, the clinical protocol constraints can be shown. Here, the user can provide a set of minimum and maximum thresholds for the ablation volume coverage of each structure. In the example at FIG. 19, the user prescribed that at least 95% of the tumor lesion must be ablated, while a maximum of 45%, 25% and 30% of the OARs' volume is ablated. Importance weights can be also set to give different importance to the prescribed constraints. The structure fractional volume values at current optimized plan are also given. Here, traffic lights can be used to highlight constraint values which are not satisfying the prescribed minimum or maximum volumetric thresholds (e.g. in red color). Additional user optimization stopping criteria could be prescribed via the GUI, e.g. maximum number of optimization iterations, the ablation objective function value tolerance, the maximum number of probes to use, etc.

As mentioned above, FIG. 24 illustrates a thermal ablation inverse planning tab. On the left side transverse, sagittal, frontal and 3D rendered images of the patient are given. Segmented structures may be delineated with different colors (blue: lesion, red: organ at risk 1 (OAR1), etc.). The optimal total ablated region is visualized and superimposed over the patient image. On the right side, on top a plot of ablated structures' volume fraction at current optimized plan is given. Column bars can be used to depict the current fraction of structure ablated volume. Arrows are used to indicate the minimum and maximum ablated volume thresholds currently prescribed in the clinical protocol. On the right-bottom part, the prescribed clinical protocol is given on the "Ablation Protocol" tab. Here, the user can prescribe minimum and maximum thresholds ("Prescribed") for the ablation volume coverage of each structure. In the example, the user prescribed that at least 95% of the tumor lesion is ablated, while a maximum 45%, 25% and 30% of the OAR1,2,3 is ablated. Importance weights can be also set to give more importance to some specific constraints. The structure fractional volumes at current optimized plan are also shown under the "Projected" column. Here, traffic lights are used to indicate constraints that don't satisfy the prescribed minimum/maximum volumetric thresholds.

Finally, at user request, the optimal sequence of ablation probes to deliver can be shown (see FIG. 20, right-bottom). All probes can be physically visualized and superimposed over the patient image at optimized positions. A specific probe selected from the listed sequence will be automatically highlighted. The list of probes can provide some geometrical and delivery information (e.g. the skin entry point, the supplier ablation zone to use, the ablation power, the delivery time, etc.). The sequence of probes to deliver could dynamically change when a 3D probe tip tracking system is available, and an adaptive real-time treatment planning and delivery workflow is applied. Here, every time a mismatch is identified between computed and delivered probe positions, a new optimization can be executed to restore the plan quality, leading to a new optimal total ablation zone and new corresponding sequence of remaining probes to deliver.

Figure 25:
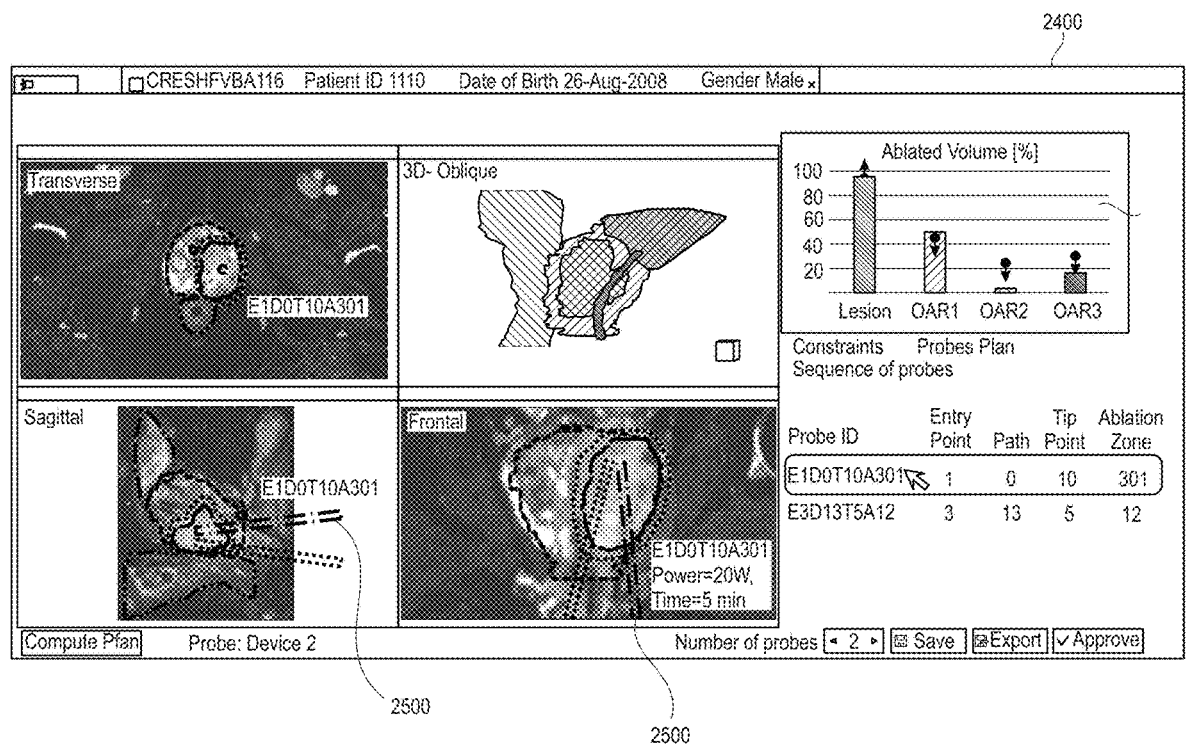
FIG. 25 illustrates a further example of a graphical user interface.

FIG. 25 shows a further view of the user interface 2400. In this example the probe insertion location 2500 has been illustrated for an operator to know where to insert the ablation probe. FIG. 25 illustrates a thermal ablation inverse planning tab. The sequence of ablation probes to deliver is shown when the user clicks on the "Probe plan" tab (right-bottom). All probes are also physically visualized superimposed over the patient image. A specific probe can be selected from the list and it will be automatically highlighted (orange color). The list of probes can provide some geometrical and delivery information (e.g. the skin entry point, the supplier ablation zone to use, the ablation power, the delivery time, etc.). The sequence of probes to deliver could dynamically change when a probe tip tracking system is available, and an adaptive real-time treatment planning and delivery workflow is applied. Here, every time a mismatch is identified between computed and executed probe positions, a new optimization can be executed to restore the plan quality, leading to a new optimal total ablation and corresponding sequence of probes yet to deliver.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
102 computer
104 processor
106 optional hardware interface
108 user interface
110 memory
112 machine executable instructions 114 three-dimensional medical image data
116 desired ablation volume
118 one or more protected volumes
120 discrete set of ablation probe positions
122 composite ablation binary mask
124 sequential ablation probe configuration list
126 unablated volume
128 chosen ablation probe configuration
130 discrete set of ablation patterns
132 chosen objective function
134 predetermined set of criteria
200 receive three-dimensional medical image data descriptive of a subject
202 receive a desired ablation volume, wherein the desired ablation volume is registered to the three-dimensional medical image data
204 receive one or more protected volumes, wherein the one or more protected volumes are registered to the three-dimensional medical image data
206 generate a discrete set of ablation probe positions registered to the three-dimensional medical image data
208 receive a discrete set of ablation patterns, wherein the discrete set of ablation patterns comprises multiple ablation patterns
210 initialize a composite ablation binary mask registered to the three-dimensional medical image data
212 initialize a sequential ablation probe configuration list
214 determining an unablated volume by comparing the composite ablation binary mask to the desired ablation volume, wherein the unablated volume is registered to the three-dimensional medical image data
216 determining a chosen ablation probe configuration using a chosen objective function dependent upon the one or more protected volumes, the unablated volume, the discrete set of ablation patterns, and the discrete set of ablation probe positions
218 update the composite ablation binary mask by calculating a union between the composite ablation binary mask and the one of the discrete set of ablation patterns located at the one of the discrete set of ablation probe positions
220 add the chosen ablation probe configuration to the sequential ablation probe configuration list
222 Are any of the predetermined set of criteria satisfied?
224 end
300 medical system
302 magnetic resonance imaging system
304 magnet
306 bore of magnet
308 imaging zone
309 field of view
310 magnetic field gradient coils
312 magnetic field gradient coil power supply
314 radio-frequency coil
316 transceiver
318 subject
320 subject support
330 pulse sequence commands
332 magnetic resonance imaging data
400 acquire the three-dimensional medical image data
500 ablation probe
502 ablation pattern
504 data descriptive of probe
506 operating conditions
600 begin
602 Generate a discrete set C of ablation device configurations
604 Initialize the set P with zero selected probes (or warm start)
606 Compute the composite ablation binary mask A
608 Compute ablation objective function values
610 select the "best" probe configuration in C and add it to the set P
612 Local refinement of selected probe configurations in the set P
614 stopping criteria satisfied?
616 end
700 ablation mask
702 ablation device configuration
800 ablated volume fraction
802 successfully ablated volume
804 remaining non-ab
900 initial ablation position
902 adjusted ablation position
902' adjusted ablation position
1100 synthetic phantom
1102 normal tissue
1104 tumor (desired ablation volume)
1106 OAR (protected volume)
1200 ablated zone within tumor
1300 ablated zone within normal tissue
1800 number of probes
1802 value of objective function F(A)
1900 fraction of ablated target
2000 fraction of ablated OAR
2100 fraction of ablated normal tissue
2200 user interface
2202 control to select list of commissioned probes
2204 control to select configuration for probe
2206 control to approve selection
2300 user interface
2302 possible skin entry points
2304 control to add entry point to list
2306 control to automatically compute look up table
2400 user interface
2402 ablated volume
2500 probe insertion location

The invention claimed is:

1. A medical system comprising:
a memory storing machine executable instructions;
a processor configured for controlling the medical system, wherein execution of the machine executable instructions causes the processor to:
receive three-dimensional medical image data descriptive of a subject;
receive a desired ablation volume, wherein the desired ablation volume is registered to the three-dimensional medical image data;
receive one or more protected volumes, wherein the one or more protected volumes are registered to the three-dimensional medical image data;
generate a discrete set of ablation probe positions registered to the three-dimensional medical image data;
receive a discrete set of ablation patterns;
initialize a composite ablation binary mask registered to the three-dimensional medical image data; and
initialize a sequential ablation probe configuration list;
wherein execution of the machine executable instructions further causes the processor to generate the sequential ablation probe configuration list by:
determining an unablated volume by comparing the composite ablation binary mask to the desired ablation volume, wherein the unablated volume is registered to the three-dimensional medical image data;

determining a chosen ablation probe configuration using a chosen objective function dependent upon the one or more protected volumes, the unablated volume, the discrete set of ablation patterns, and the discrete set of ablation probe positions, wherein the chosen ablation probe configuration specifies one of the discrete set of ablation probe positions and one of the discrete set of ablation patterns;

update the composite ablation binary mask by calculating a union between the composite ablation binary mask and the one of the discrete set of ablation patterns located at the one of the discrete set of ablation probe positions; and add the chosen ablation probe configuration to the sequential ablation probe configuration list; and wherein execution of the machine executable instructions further causes the processor to repeatedly generate the sequential ablation probe configuration list until one or more of a predetermined set of criteria is satisfied.

2. The medical system of claim 1, wherein execution of the machine executable instruction further causes the processor to update the sequential ablation probe configuration list by iteratively:

assigning each of the one of the discrete set of ablation probe positions to a spatially continuous probe position; and modifying the spatially continuous probe position using a second objective function.

3. The medical system of claim 2, wherein the spatially continuous probe position is a spatially continuous linear position and/or a spatially continuous rotation.

4. The medical system of claim 1, wherein the medical system further comprises a display, wherein execution of the machine executable instructions further causes the processor to display the sequential ablation probe configuration list on the display.

5. The medical system of claim 4, wherein the sequential ablation probe configuration list is displayed as any one of the following:

a list of grid locations and insertion depths for an indexed ablation probe insertion block; and an illustration of ablation probes specified in the sequential ablation probe configuration list.

6. The medical system of claim 4, wherein the medical system further comprises a medical imaging system configured for acquiring the three-dimensional medical image data, wherein execution of the machine executable instructions further causes the processor to control the medical imaging system to acquire the three-dimensional medical image data.

7. The medical system of claim 6, wherein the medical imaging system is any one of the following: a magnetic resonance imaging system, an ultrasound system, a computed tomography system, and combinations thereof.

8. The medical system of claim 6, wherein execution of the machine executable instructions further causes the processor to:

control the medical imaging system to acquire real-time ablation probe tracking data;

determine an ablation probe position registered to the three-dimensional medical image data using the real-time ablation probe tracking data; and render the ablation probe position superimposed on the three-dimensional medical image data using the display in real time.

9. The medical system of claim 8, wherein execution of the machine executable instructions further causes the processor to:

determine a measured position for the chosen ablation probe configuration of the sequential ablation probe configuration list, and recalculate the sequential ablation probe configuration list using the measured position as a fixed position.

10. The medical system of claim 6, wherein execution of the machine executable instructions further causes the processor to:

measure an ablated volume using the medical imaging system, correct the desired ablation volume by removing the ablation volume from the desired ablation volume; and recalculate the sequential ablation probe configuration list using the corrected desired ablation volume.

11. The medical system of claim 1, wherein the chosen objective function comprises a quadratic ablation coverage-based objective function, a minimum/maximum ablation coverage function, and a uniform quadratic coverage function.

12. The medical system of claim 1, wherein the predetermined set of criteria comprises any one of the following:

a maximum number of allowed ablation probes;

an ablation coverage goal of the desired ablation volume; and combinations thereof.

13. The medical system of claim 1, wherein the discrete set of ablation patterns comprises ablation patterns for any one of the following:

cryo-ablation probe ablation patterns;

laser ablation probe ablation patterns;

microwave ablation probe ablation patterns;

focused ultrasound ablation probe ablation patterns;

radio-frequency ablation probe ablation patterns;

irreversible electroporation probe ablation patterns; and combinations thereof.

14. A computer program product comprising machine executable instructions for execution by a processor controlling a medical system, wherein execution of the machine executable instructions causes the processor to:

receive three-dimensional medical image data descriptive of a subject;

receive a desired ablation volume, wherein the desired ablation volume is registered to the three-dimensional medical image data;

receive one or more protected volumes, wherein the one or more protected volumes are registered to the three-dimensional medical image data;

generate a discrete set of ablation probe positions registered to the three-dimensional medical image data;

receive a discrete set of ablation patterns; and initialize a composite ablation binary mask registered to the three-dimensional medical image data;

initialize a sequential ablation probe configuration list;

wherein execution of the machine executable instructions further causes the processor to generate the sequential ablation probe configuration list by:

determining an unablated volume by comparing the composite ablation binary mask to the desired ablation volume, wherein the unablated volume is registered to the three-dimensional medical image data;

determining a chosen ablation probe configuration using a chosen objective function dependent upon the one or more protected volumes, the unablated volume, the discrete set of ablation patterns, and the discrete set of ablation probe positions, wherein the chosen ablation probe configuration specifies one of the discrete set of ablation probe positions and one of the discrete set of ablation patterns;

update the composite ablation binary mask by calculating a union between the composite ablation binary mask and the one of the discrete set of ablation patterns located at the one of the discrete set of ablation probe positions; and add the chosen ablation probe configuration to the sequential ablation probe configuration list; and wherein execution of the machine executable instructions further causes the processor to repeatedly generate the sequential ablation probe configuration list until one or more of a predetermined set of criteria is satisfied.

15. A method of operating a medical system, wherein the method comprises:

generating a discrete set of ablation probe positions registered to three-dimensional medical image data;

initializing a composite ablation binary mask registered to the three-dimensional medical image data;

initializing a sequential ablation probe configuration list;

determining an unablated volume by comparing the composite ablation binary mask to a desired ablation volume, wherein the unablated volume is registered to the three-dimensional medical image data;

determining a chosen ablation probe configuration using a chosen objective function dependent upon one or more protected volumes, the unablated volume, a discrete set of ablation patterns, and the discrete set of ablation probe positions, wherein the chosen ablation probe configuration specifies one of the discrete set of ablation probe positions and one of the discrete set of ablation patterns;

updating the composite ablation binary mask by calculating a union between the composite ablation binary mask and the one of the discrete set of ablation patterns located at the one of the discrete set of ablation probe positions; and adding the chosen ablation probe configuration to the sequential ablation probe configuration list; and wherein the sequential ablation probe configuration list is repeatedly generated until one or more of a predetermined set of criteria is satisfied.

* * * * *